US006965661B2

(12) United States Patent
Kojima et al.

(10) Patent No.: US 6,965,661 B2
(45) Date of Patent: Nov. 15, 2005

(54) RADIOLOGICAL IMAGING APPARATUS AND RADIOLOGICAL IMAGING METHOD

(75) Inventors: Shinichi Kojima, Hitachi (JP); Kikuo Umegaki, Hitachinaka (JP); Takashi Okazaki, Hitachinaka (JP); Kensuke Amemiya, Hitachinaka (JP); Hiroshi Kitaguchi, Naka (JP); Yuuichirou Ueno, Hitachi (JP)

(73) Assignee: Hitachi, Ltd., Tokyo (JP)

( * ) Notice: Subject to any disclaimer, the term of this patent is extended or adjusted under 35 U.S.C. 154(b) by 0 days.

(21) Appl. No.: 10/098,593

(22) Filed: Mar. 18, 2002

(65) Prior Publication Data

US 2002/0191734 A1 Dec. 19, 2002

(30) Foreign Application Priority Data

Jun. 19, 2001 (JP) .......................... 2001-184206
Sep. 12, 2001 (JP) .......................... 2001-275897

(51) Int. Cl.$^7$ .......................................... G01N 23/083
(52) U.S. Cl. .............................. 378/4; 378/10; 378/19
(58) Field of Search ................... 378/4, 98.8, 96, 378/155, 11, 10, 193–197, 63, 15, 19; 250/363.04, 363.02, 363.03, 370.06, 370.09; 600/427

(56) References Cited

U.S. PATENT DOCUMENTS

| | | | |
|---|---|---|---|
| 4,220,863 A | | 9/1980 | McBride et al. |
| 4,592,080 A | | 5/1986 | Rauch et al. |
| 5,600,145 A | | 2/1997 | Plummer |
| 5,666,391 A | * | 9/1997 | Ohnesorge et al. ............ 378/7 |
| 6,118,839 A | | 9/2000 | Dafni et al. |
| 6,212,251 B1 | * | 4/2001 | Tomura et al. ............... 378/15 |
| 6,332,014 B1 | * | 12/2001 | Boutenko et al. ............. 378/95 |
| 6,448,559 B1 | * | 9/2002 | Saoudi et al. ............... 250/367 |
| 6,449,331 B1 | * | 9/2002 | Nutt et al. .................... 378/19 |
| 6,490,476 B1 | * | 12/2002 | Townsend et al. .......... 600/427 |
| 2003/0118155 A1 | * | 6/2003 | Ueno et al. ................. 378/177 |

FOREIGN PATENT DOCUMENTS

| | | |
|---|---|---|
| JP | 4-263839 | 9/1992 |
| JP | 5-302979 | 11/1993 |
| JP | 7-20245 | 1/1995 |
| JP | 9-5441 | 1/1997 |
| JP | 09-10204 | 1/1997 |
| JP | 2000-107162 | 4/2000 |
| JP | 2000-180550 | 6/2000 |
| JP | 2001-17420 | 1/2001 |

OTHER PUBLICATIONS

IEEE Transactions on Nuclear Science, NS–21, 1974, pp. 228–229.
Saoudi, A., et al, "A Novel APD–Based Detector Module for Multi–Modality PET/SPECT/CT Scanners", IEEE, Nuclear Science Symposium Conf., Toronto, CA, Nov. 8–14, 1998, vol. 1, Nov. 8, 1998, pp. 1089–1094.
Lang, T.F., et al, "A Prototype Emission–Transmission Imaging System", IEEE, Nuclear Science Symposium and Medical Imaging Conf., Santa Fe, Nov. 2–9, 1991, vol. 1, Nov. 2, 1991, p. 1902.

* cited by examiner

Primary Examiner—David V. Bruce
Assistant Examiner—Hoon Song
(74) Attorney, Agent, or Firm—Mattingly, Stanger, Malur & Brundidge, P.C.

(57) ABSTRACT

An image pickup apparatus of a radiological imaging apparatus includes a plurality of radiation detectors arranged in a ring form around a through hole section formed on a casing into which an examinee is inserted. An X-ray source unit having an X-ray source moves in a circumferential direction of the through hole section along a ring-shaped guide rail provided on the casing. Each radiation detector outputs both an X-ray detection signal which is a detection signal of X-rays that have passed through the examinee and a γ-ray detection signal which is a detection signal of γ-rays radiated from the examinee caused by radiopharmaceutical. A computer creates an X-ray computed tomographic image data based on the X-ray detection signal and a PET image data based on the γ-ray detection signal and creates fused tomographic image data using the X-ray computed tomographic image data and the PET image data.

27 Claims, 20 Drawing Sheets

FIG. 9A  RADIATION DETECTOR TIME WINDOW 
FIG. 9B  DETECTION SIGNAL OF RADIATION DETECTOR 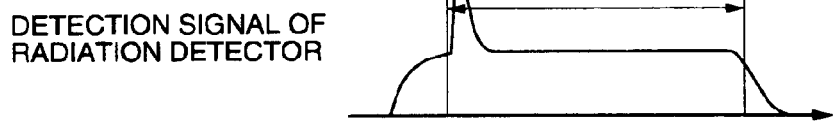
FIG. 9C  γ-RAY IMAGE PICKUP SIGNAL 
FIG. 9D  X-RAY IMAGE PICKUP SIGNAL 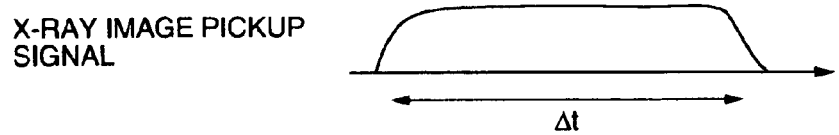

RADIOLOGICAL IMAGING APPARATUS AND RADIOLOGICAL IMAGING METHOD

BACKGROUND OF THE INVENTION

The present invention relates to a radiological imaging apparatus and radiological imaging method, and more particularly, to a radiological imaging apparatus and radiological imaging method ideally applicable to positron emission computed tomography (hereinafter referred to as "PET") and single photon emission computer tomography (hereinafter referred to as "SPECT").

Radiological imaging is a non-invasive imaging technology to examine physical functions and conformation of a medical examinee. Among typical radiological imaging methods using radiation are X-ray computed tomography, PET and SPECT, etc. X-ray computed tomography irradiates an examinee with radioactive rays radiated from an X-ray source and picks up images of the physical conformation based on the transmittance of radioactive rays in the body of the examinee. Detecting the intensity of X-rays passing through the body using a radiation detector makes it possible to calculate a linear attenuation coefficient between the X-ray source and the radiation detector. From this linear attenuation coefficient, a linear attenuation coefficient of each voxel is calculated using a filtered back projection method described in the IEEE Transactions on Nuclear Science NS volume 21 (issued in 1974, pp.228–229) and this value is converted to a CT value. The radiation source often used for X-ray computed tomography is approximately 80 keV.

PET is a method consisting of administering radiopharmaceutical (hereinafter referred to as "PET radiopharmaceutical") including matters having a property of concentrating on positron radiateters ($^{15}O$, $^{13}N$, $^{11}C$, $^{18}F$, etc.) and specific cells in the body to the examinee and examining locations in the body where more PET radiopharmaceutical are consumed. One positron emitted from a positron radiateter in the PET radiopharmaceutical couples with an electron of a neighboring cell to disappear and irradiates a pair of γ-rays (γ-ray pair) having energy of 511 keV. These γ-rays are radiated in directions opposite to each other. Detecting this pair of γ-rays using a radiation detector makes it possible to know between which radiation detectors the positron is emitted. Detecting those many γ-ray pairs makes it possible to identify locations where more PET radiopharmaceutical are consumed. For example, when PET radiopharmaceutical including positron radiateters are created using carbohydrate as a matter having a property of concentrating on a specific cell, these PET radiopharmaceutical concentrate on cancer cells having hyperactive carbohydrate metabolism. This makes it possible to discover cancer focuses. The data obtained is converted to radiation density of each voxel using a method such as the aforementioned Filtered Back Projection. $^{15}O$, $^{13}N$, $^{11}C$ and $^{18}F$ used for the PET are radioisotopes with a short half life of 2 to 110 minutes.

The SPECT administers radiopharmaceutical (hereinafter referred to as "SPECT radiopharmaceutical") including single photon radiateters to an examinee and detects γ-rays radiated from the radiateters using a radiation detector. The energy of γ-rays radiated from the single photon radiateters often used for inspection using the SPECT is around several 100 keV. In the case of the SPECT, single γ-rays are radiated, and therefore it is not possible to obtain their angle of incidence upon the detector. Thus, angle information is obtained by detecting only γ-rays incident from a specific angle using a collimator. The SPECT administers SPECT radiopharmaceutical including a matter having a property of concentrating on a specific tumor or molecule and single photon radiateters ($^{99}Tc$, $^{67}Ga$, $^{201}Tl$, etc.) to the examinee, detects γ-rays generated by the SPECT radiopharmaceutical and identifies locations where more SPECT radiopharmaceutical are consumed. The SPECT also converts data obtained to data of each voxel using a method such as Filtered Back Projection. The SPECT often takes transmission images, too. $^{99}Tc$, $^{67}Ga$ and $^{201}Tl$ used for the SPECT have a half life longer than that of radioisotopes used for the PET, for example, 6 hours to 3 days.

The aforementioned conventional inspections are carried out independently of one another. Inspections using the PET and SPECT make it possible to know a distribution of the amount of consumption of radiopharmaceutical within an image pickup apparatus. However, because of the absence of information on the correspondence with the physical locations of an examinee, the detailed position of the focus may remain unidentified. Thus, coupling of a PET image or SPECT image with an X-ray computed tomographic image that can identify locations in the body of the examinee is being practiced in recent years. An example of such a radiological imaging apparatus is described in JP-A-7-20245. That is, the radiological imaging apparatus places the image pickup apparatus of the X-ray computed tomographic apparatus and that of the PET apparatus side by side close to each other in parallel to realize quasi-simultaneous imaging. The examinee is laid down on a bed of an examinee holding apparatus and sequentially moved inside both image pickup apparatuses through horizontal movements of the bed. Pictures of the examinee are taken by the image pickup apparatus of the X-ray computed tomographic apparatus and then by the image pickup apparatus of the PET apparatus. In this case, since the time interval between two imaging operations is short and the examinee hardly moves on the bed, it is possible to know a correlation between the PET data and X-ray computed tomographic data, the image data taken by the two image pickup apparatuses. The PET data is coupled with the X-ray computed tomographic data using the information on the correlation and the focus location of the examinee is identified in this way.

JP-A-9-5441 describes a radiological imaging apparatus which also serves as a bed with an image pickup apparatus of an X-ray computed tomographic apparatus placed in parallel just next to an image pickup apparatus of a SPECT apparatus. The X-ray computed tomographic data and the SPECT data which are the image data taken by those image pickup apparatuses are coupled to identify the focus location of the examinee.

The radiological imaging apparatuses described in the above-described publications apparently present a clear positional relationship between two image data pieces, but there is a possibility that the examinee will move between both image pickup apparatuses. Resolution of an image pickup apparatus of a recent PET apparatus is approximately 5 mm and resolution of an image pickup apparatus of an X-ray computed tomographic apparatus is approximately 0.5 mm, an order of magnitude smaller. Because of this, if the examinee moves between both image pickup apparatuses or the angle of the examinee changes, the correlation between image data pieces taken by both image pickup apparatuses becomes unclear. As a result, after reconstructing image data pieces into an image, it is necessary to extract characteristic areas that exist commonly in different images, find a positional relationship between those images from the positional relationship of the characteristic areas and perform positioning on those images. Furthermore, equipped with two image pickup apparatuses each provided with a radiation detector, etc., these radiological imaging apparatuses have a complicated apparatus configuration.

SUMMARY OF THE INVENTION

It is an object of the present invention to provide a radiological imaging apparatus and radiological imaging method in a simplified apparatus configuration.

A feature of the present invention to attain the above-described object is that it is provided with a plurality of radiation detectors that output a first detection signal which is the detection signal of X-rays passing through an examinee and a second detection signal which is the detection signal of γ-rays radiated from the examinee. Since each radiation detector outputs the first detection signal and second detection signal, the radiological imaging apparatus equipped with the radiation detector has an apparatus configuration significantly simplified compared to the conventional radiological imaging apparatus equipped with an image pickup apparatus provided with a plurality of radiation detectors to detect X-rays passing through an examinee and another image pickup apparatus provided with a plurality of radiation detectors to detect γ-rays radiated from the examinee. The radiological imaging apparatus is an apparatus for inspecting an examinee using radioactive rays.

It is preferable that the radiological imaging apparatus include a tomographic image data creation apparatus that creates first tomographic image data of an examinee based on the first detection signal, creates second tomographic image data of the examinee based on the second detection signal and creates fused tomographic image data combining the first tomographic image data and the second tomographic image data.

Another feature of the present invention attaining the above-described object is that the image pickup apparatus includes a radiation detector ring structure consisting of a plurality of radiation detectors arranged in a ring form for detecting radiation from the examinee, an X-ray source that irradiates the examinee with X-rays and an X-ray source transfer apparatus that transfers the X-ray source in the circumferential direction of the radiation detector ring structure. With a plurality of radiation detectors arranged in a ring form, it is possible to detect a plurality of γ-ray pairs radiated from the examinee and also detect X-rays which are radiated from the X-ray source moving in the circumferential direction and passing through the examinee. This simplifies the configuration of the radiological imaging apparatus.

It is preferable that the X-ray source be placed outside the above-described radiation detector ring structure.

BRIEF DESCRIPTION OF THE DRAWINGS

FIGS. 9A–9D are operation time charts of the signal discriminator in FIG. 8;

DETAILED DESCRIPTION OF THE EMBODIMENTS (Embodiment 1)

Figure 1:
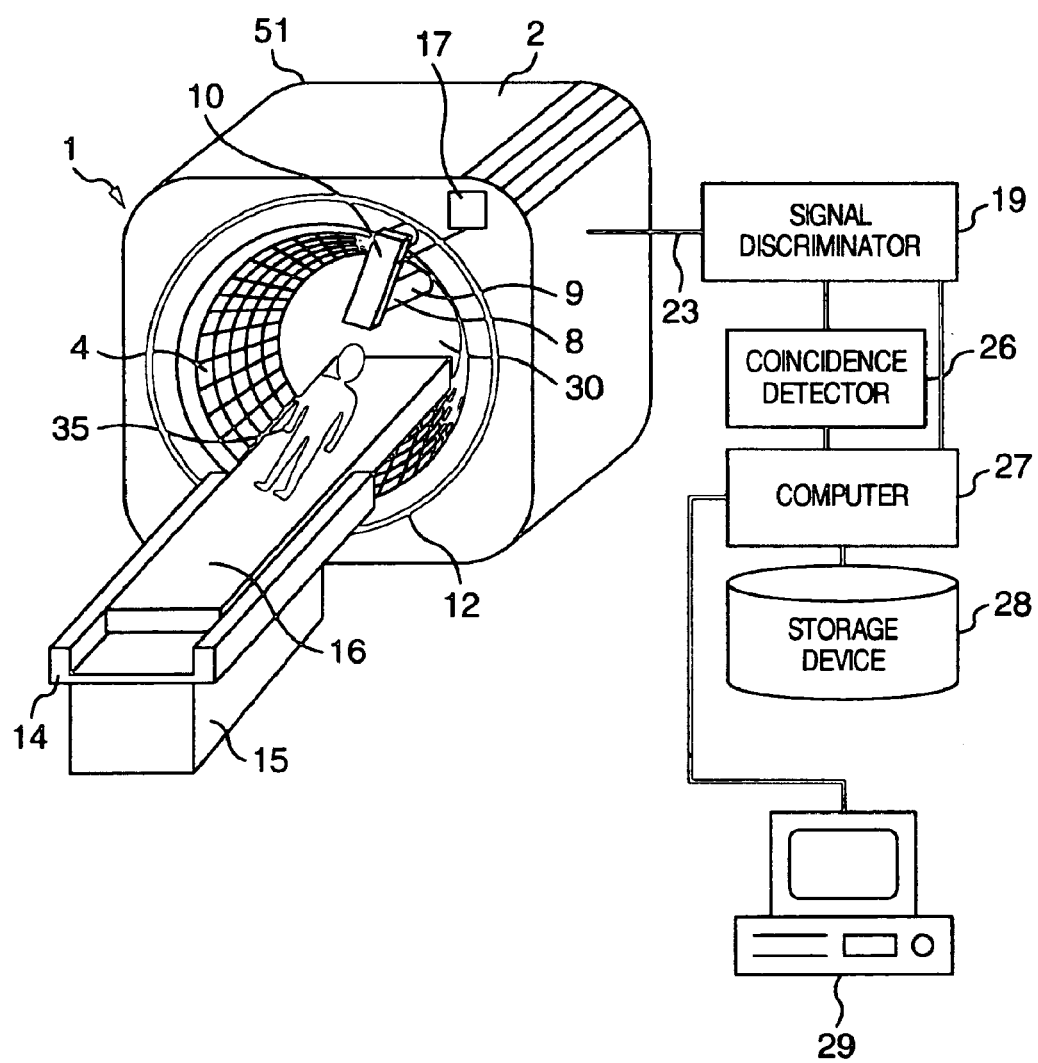
FIG. 1 is a perspective view of a radiological imaging apparatus which is a preferred embodiment of the present invention.
Figure 2:
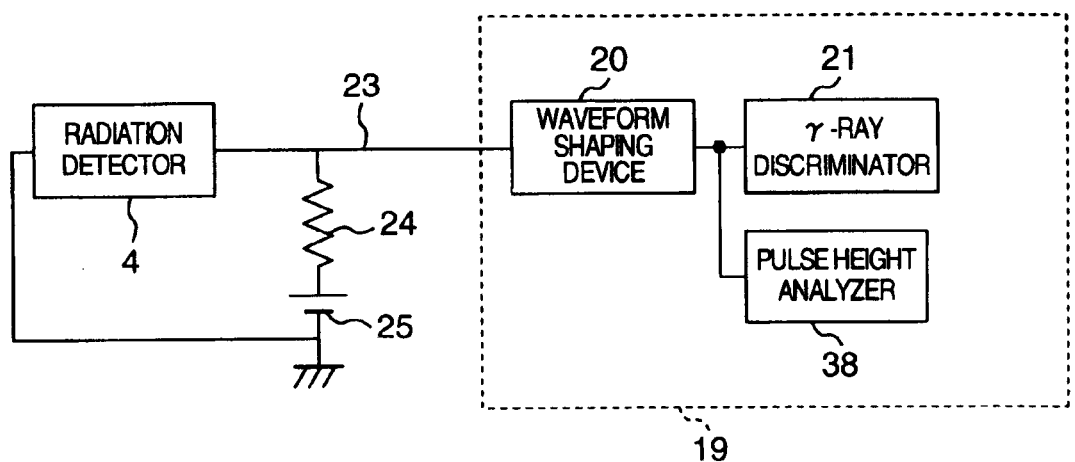
FIG. 2 is a bock diagram of a signal discriminator in the embodiment shown in FIG. 1.

With reference now to FIG. 1 and FIG. 2, a radiological imaging apparatus which is a preferred embodiment of the present invention will be explained below. A radiological imaging apparatus 1 of this embodiment is provided with an image pickup apparatus 2, an examinee holding apparatus 14, a signal discriminator 19, a coincidence detector 26, a storage device 28, a computer 27 and a display device 29. The examinee holding apparatus 14 includes a support 15 and a bed installed on top of the support 15 in a manner movable in a longitudinal direction. The image pickup apparatus 2 includes radiation detectors 4, a casing 15 provided with a through hole section 30, an X-ray source apparatus 8, a guide rail 12 and a drive controller 17. The image pickup apparatus 2 is installed in a direction perpendicular to the longitudinal direction of the bed 16. The radiation detector 4 is a semiconductor radiation detector. Many radiation detectors 4 (10000 in total) are set in the casing 15 arranged surrounding the through hole section 30 into which the examinee 35 is inserted. That is, an array of ring-shaped radiation detectors in which many radiation detectors 4 are placed in the circumferential direction of the through hole section 30 is formed. A plurality of arrays of ring-shaped radiation detectors are placed in the axial direction of the through hole section 30, that is, the longitudinal direction of the bed 16 forming a radiation detector ring structure.

The semiconductor device constituting the detection section of the radiation detectors 4 consists of cadmium telluride (CdTe), gallium arsenide (GaAs) or cadmium zinc telluride (CZT), etc.

The X-ray source apparatus 8 is provided with an X-ray source 9 and an X-ray source drive 10. The X-ray source drive 10 is provided with a motor and a power transmission mechanism including a reduction gear mechanism inside the casing 15 though all these are not shown. The power transmission mechanism is connected with the motor. The X-ray source 9 is attached to the casing of the X-ray source drive 10 and extends toward the inside of the through hole section 30. The ring-shaped guide rail 12 is set on the side wall facing the examinee holding apparatus 14 of the casing 15 in such a way as to surround the through hole section 30. The X-ray source drive 10 is attached to the guide rail 12 in such a way as not to fall and to be movable along the ring-shaped guide rail 12. The X-ray source drive 10 has a pinion (not shown) to receive a rotational force from the aforementioned power transmission mechanism. This pinion engages with a rack provided for the guide rail 12.

The signal discriminator 4 is provided with a waveform shaping device 20, a γ-ray discriminator 21 and a pulse height analyzer 38. The signal discriminator 4 is connected to the radiation detector 2 via wiring 23. The signal discriminator 19 is provided one for each radiation detector 4. The wiring 23 is connected to the waveform shaping device 20 of the signal discriminator 19. The γ-ray discriminator 21 and the pulse height analyzer 38 are connected to the waveform shaping device 20. The γ-ray discriminator 21 is connected to the computer 27 via the coincidence detector 26. The number of the coincidence detectors 26 is one and connected to all the γ-ray discriminators 21. The coincidence detector 26 can also be provided for several γ-ray discriminators 21. Each pulse height analyzer 38 is connected to the computer 27. The storage device 28 and the display device monitor 29 are connected to the computer 27. A minus terminal of a power supply 25 is connected to the wiring 23 via a resistor 24 and a plus terminal of the power supply 25 is connected to the radiation detector 4. The signal discriminator 19 is a signal processor. This signal processor is provided with a first signal processor including the pulse height analyzer 38 and a second signal processor including the waveform shaping device 20 and γ-ray discriminator 21.

This embodiment shows an example of performing an X-ray computed tomographic inspection (action of detecting X-rays radiated from the X-ray source 9 and passing through the body of the examinee using the radiation detector) and an PET inspection (action of detecting γ-rays radiated from within the body of the examinee 35 caused by PET radiopharmaceutical using the radiation detector) using one image pickup apparatus 2.

Before starting an inspection, a PET radiopharmaceutical is administered into the body of the examinee 35 by means of an injection, etc. and the system waits for a predetermined time until the PET radiopharmaceutical is spread inside the body to make image taking possible and concentrated on the affected area. The PET radiopharmaceutical is selected according to the affected area to be inspected. After a lapse of the predetermined time, the PET radiopharmaceutical is concentrated on the affected area (e.g., the area affected by cancer) of the examinee 35. After the lapse of the predetermined time, the examinee 35 is laid down on the bed 16 of the examinee holding apparatus 14.

When pictures of the examinee 35 are taken using the image pickup apparatus 2, the bed 16 is moved toward the image pickup apparatus 2. The examinee 35 on the bed 16 and the bed 16 are inserted into the through hole section 30 and move in the opposite direction. The 511 keV γ-rays radiated from the affected area in the body of the examinee 35 are introduced into the radiation detector 4. On the other hand, the X-rays having a certain energy level irradiated from the X-ray source 9 pass through the examinee 35 and then enter the radiation detector 4. The energy of the X-rays is 80 keV, for example. During a X-ray CT inspection, the X-ray source apparatus 8 is moved around the examinee 35 along the guide rail 12, and therefore the examinee 35 is irradiated with X-rays from the X-ray source 9 from all positions in the circumferential direction. When the X-ray source apparatus 8 is moved along the guide rail 12 at the start of an X-ray computed tomographic inspection, the drive controller 17 outputs a drive start signal and closes a switch for a power supply connected to the motor of the X-ray source drive 10. With a supply of current, the motor rotates and the rotational force is transmitted to the pinion via the power transmission mechanism, making the pinion rotate. Since the pinion is engaged with the rack of the guide rail 50, the X-ray source apparatus 8 moves along the guide rail 12 in the circumferential direction. The X-ray source 9 moves around the examinee 35 inserted in the through hole section 30. When the X-ray computed tomographic inspection is finished, the drive controller 17 outputs a drive stop signal and opens the above-described switch.

Each radiation detector 4 detects the X-rays radiated from the X-ray source 9 and passing through the body of the examinee 35 and the γ-rays radiated from the affected area caused by the PET radiopharmaceutical. Then, each radiation detector 4 outputs an output signal including both a detection signal of X-rays passing through the body (hereinafter referred to as "X-ray image pickup signal") and a detection signal of γ-rays (hereinafter referred to as "γ-ray image pickup signal"). This output signal is also an image pickup signal and input to the corresponding signal discriminator 19 via the corresponding wiring 23. The power supply 25 applies a voltage to the radiation detector 4 to actuate the radiation detector 4. Since the application of the voltage produces an electric field in the semiconductor device of the radiation detector 4, the X-rays and γ-rays incident upon the semiconductor device generate charges in the semiconductor device. These charges are output from the radiation detector 4 as image pickup signals.

The function of the signal discriminator 19 will be explained below. The signal discriminator 19 has the function of separating an X-ray image pickup signal and γ-ray image pickup signal from the output signal of the radiation detector 4. That is, the signal discriminator 19 is an apparatus to discriminate the X-ray image pickup signal and γ-ray image pickup signal detected from one radiation detector 4 by energy. The time interval at which the X-ray source 9 irradiates X-rays is longer than an operating time window Δτ of the signal discriminator 19.

Figure 3:
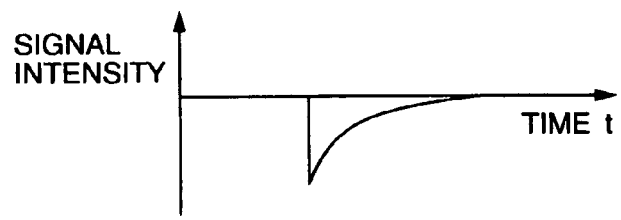
FIG. 3 illustrates a waveform of a γ-ray image pickup signal input to a waveform shaping apparatus in FIG. 2.
Figure 4:
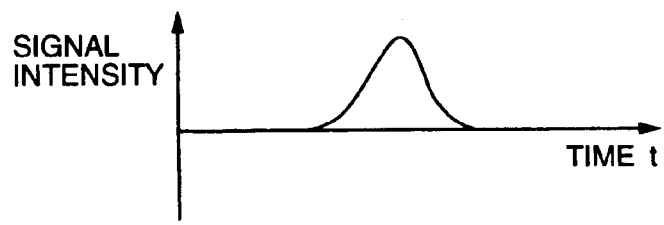
FIG. 4 illustrates a waveform of a γ-ray image pickup signal output from the waveform shaping apparatus in FIG. 2.

The waveform shaping device 20 of the signal discriminator 19 is fed the output signal from the radiation detector 4. The γ-ray image pickup signal entered falls abruptly in the beginning and then comes closer to 0 at an exponential rate as shown in FIG. 3. The γ-ray discriminator 21 which is fed the output signal of the waveform shaping device 20 cannot process the γ-ray image pickup signal with the waveform shown in FIG. 3. For this reason, the waveform shaping device 20 converts the γ-ray image pickup signal having the waveform shown in FIG. 3 to a waveform of a Gaussian distribution on the time axis as shown in FIG. 4 and outputs the signal. The waveform of the X-ray image pickup signal detected by the radiation detector 4 is also shaped to a Gaussian distribution by the waveform shaping device 20 and output.

The γ-ray image pickup signal and X-ray image pickup signal output from the waveform shaping device 20 are input to the γ-ray discriminator 21 and pulse height analyzer 38. The γ-ray discriminator 21 needs to process the γ-ray image pickup signal, while the pulse height analyzer 38 needs to process the X-ray image pickup signal. Thus, this embodiment adopts the following feature.

As described above, the energy of the γ-rays produced by annihilation of positrons emitted from the PET radiopharmaceutical in the body is 511 keV. However, all the energy of the γ-rays is not always changed to charges in the semiconductor device of the radiation detector 4. Thus, the γ-ray discriminator 21 uses energy of 450 keV, which is lower than 511 keV as an energy set value and generates a pulse signal having predetermined energy when an image pickup signal having energy equal to or greater than this energy set value (called "first energy set value") is input. That is, the γ-ray discriminator 21 is an apparatus that generates a pulse signal having the above-described energy when an image pickup signal (γ-ray image pickup signal) equal to or greater than the first energy set value is input.

When an image pickup signal (X-ray image pickup signal) output from the waveform shaping device 20 having energy lower than the first energy set value is input, the pulse height analyzer 38 measures the count rate of the image pickup signal. Since, the energy of the X-rays irradiated onto the examinee 35 is 80 keV in this embodiment, the pulse height analyzer 38 counts an image pickup signal (X-ray image pickup signal) having energy ranging from 70 keV which is the second energy set value to 90 keV which is the third energy set value and outputs the count rate of the image pickup signal. Processing such an image pickup signal with such specific energy reduces the load on the pulse height analyzer 38 significantly.

As described above, in order for the γ-ray discriminator 21 and pulse height analyzer 38 to process image pickup signals having specific energy, it is preferable to provide a filter that allows an image pickup signal within a predetermined energy range to pass inside the γ-ray discriminator 21 and pulse height analyzer 38 (or before the γ-ray discriminator 21 and pulse height analyzer 38). A first filter is provided inside the γ-ray discriminator 21 to allow an image pickup signal having energy equal to or greater than the first energy set value to pass and block an image pickup signal having energy lower than the set value. The γ-ray discriminator 21 generates a pulse signal for the image pickup signal that has passed through the first filter. A second filter is provided inside the pulse height analyzer 38 to allow an image pickup signal having energy ranging from the second energy set value to the third energy set value to pass and block an image pickup signal having energy outside the range. The pulse height analyzer 38 counts the image pickup signals (X-ray image pickup signals) that have passed through the second filter.

Using the signal discriminator 19, this embodiment can separate the γ-ray image pickup signal and x-ray image pickup signal having different energy corresponding to a peak count rate from the image pickup signal which is the output of the radiation detector 4.

The coincidence detector 26 is fed a pulse signal output from the γ-ray discriminator 21 of each signal discriminator 19, performs coincident counting using these pulse signals and calculates a count rate corresponding to the γ-ray image pickup signal. Furthermore, the coincidence detector 26 datarizes the two detection points where a pair of γ-rays are detected by a pair of pulse signals corresponding to the aforementioned pair of γ-rays (the positions of a pair of radiation detectors 4) as position information of the γ-ray detection.

Figure 5:
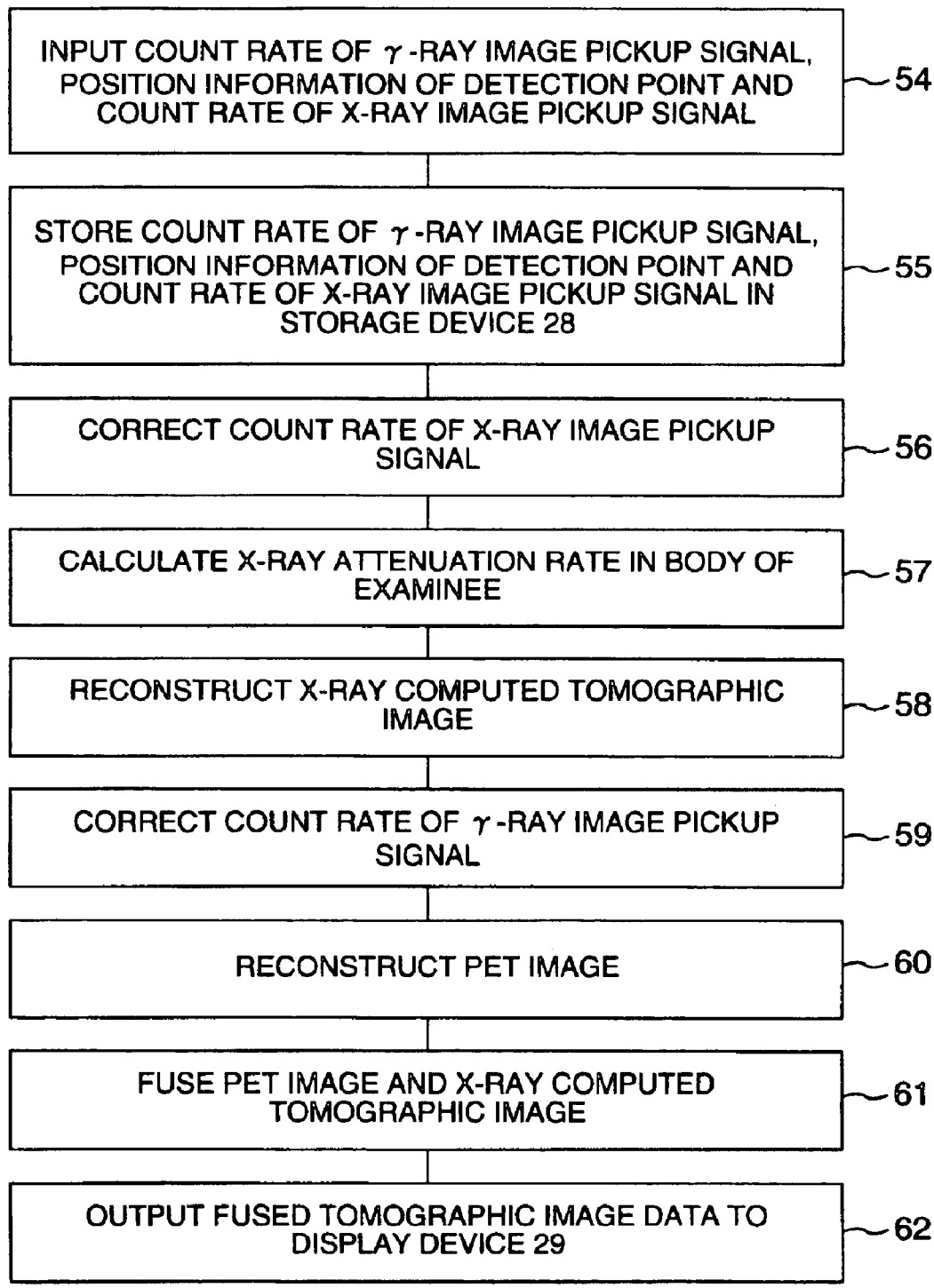
FIG. 5 is a flow chart of a procedure executed by a computer in FIG. 1.

The computer 27 carries out processing based on the procedure in steps 54 to 62 in FIG. 5. The computer 27 carrying out such processing is an apparatus for creating tomographic image data. The count rate of the γ-ray image pickup signal counted by the coincidence detector 26, position information of the detection point output from the coincidence detector 26, position information of the detection point output from the coincidence detector 26 and the count rate of the X-ray image pickup signal output from the pulse height analyzer 38 are input (step 54). The count rate of the γ-ray image pickup signal, position information of the detection point and count rate of the X-ray image pickup signal which have been input are stored in the storage device 28 (step 55).

Then, the count rate of the X-ray image pickup signal is corrected in step 56. This correction will be explained in further detail below.

Figure 6:
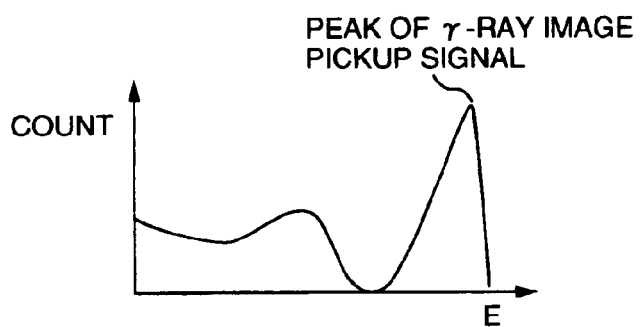
FIG. 6 illustrates an energy spectrum of a γ-ray image pickup signal detected by a radiation detector.
Figure 7:
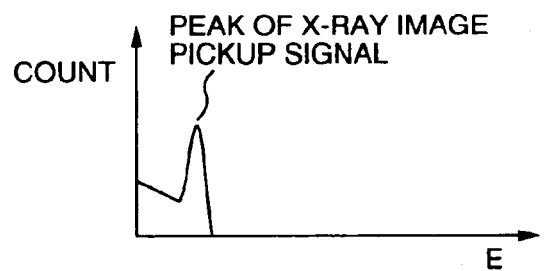
FIG. 7 illustrates an energy spectrum of an X-ray image pickup signal stripped of the γ-ray image pickup signal.

The energy of the X-rays irradiated onto the examinee 35 is 80 keV as described above and is energy lower than that of the γ-rays generated in the body caused by the PET radiopharmaceutical. The count rate of the X-ray image pickup signal output from the pulse height analyzer 38 includes the count rate of the γ-ray image pickup signal whose energy has attenuated around 80 keV inside the semiconductor device. Therefore, a count rate of a true X-ray image pickup signal is calculated by performing correction that removes the count rate of the γ-ray image pickup signal from the count rate of the X-ray image pickup signal. An example of a method of correcting the count rate of the X-ray image pickup signal will be explained. For example, a spectrum of detected γ-ray of 511 keV is measured beforehand and the intensity of the γ-ray around 80 keV is estimated using the measurement result of this detected spectrum. Suppose the spectrum as shown in FIG. 6 is obtained when the semiconductor device of the radiation detector 2 is irradiated with 511 keV γ-rays. Then, suppose 100 γ-rays radiated from within the body of the examinee 7 are detected by a certain semiconductor device. In this case, after multiplying count rates of all the spectrum shown in FIG. 6 by an equal value so that the count rate at a peak part in FIG. 6 is 100, subtracting the equimultiplied count rate from the count rate of the X-ray image pickup signal obtains an accurate count rate of a single X-ray image pickup signal as shown in FIG. 7. This corrected count rate is stored in the storage device 28.

The intensity is calculated using the corrected count rate of the X-ray image pickup signal stored in the storage device 28 and an attenuation rate of X-rays in each voxel in the body of the examinee 35 is calculated (step 57). This attenuation rate and intensity of the X-ray image pickup signal are stored in the storage device 28.

The tomography of a cross section of the examinee 35 is reconstructed using the attenuation rate of the X-ray image pickup signal at the corresponding position (step 58). The intensity of an X-ray image pickup signal, that is, a tomography reconstructed using the attenuation rate of an X-ray image pickup signal is called an "X-ray computed tomographic image". To reconstruct an X-ray computed tomographic image, a linear attenuation coefficient in the body of an attenuation between the X-ray source 9 and the semiconductor device of the radiation detector 4 that has detected the X-rays is calculated using the attenuation rate of the X-ray image pickup signal read from the storage device 28. Using this linear attenuation coefficient, a linear attenuation coefficient of each voxel is calculated according to the filtered back projection method. Using the value of the linear attenuation coefficient of each voxel, a CT value at each voxel is calculated. Using these CT values, X-ray computed tomographic image data is obtained. This X-ray computed tomographic image data is stored in the storage device 29.

Since γ-rays generated in an affected area are absorbed or attenuated while the γ-rays are passing through the body, it is also possible to estimate these effects from the aforementioned attenuation rate data, correct the count rate of the γ-ray image pickup signal and thereby obtain a count rate of the γ-ray image pickup signal more accurately. In step 59, a count rate of the γ-ray image pickup signal is corrected. An example of the correction method regarding the count rate of the γ-ray image pickup signal will be described below. First, a tomography of the examinee 7 is reconstructed using the attenuation rate of the X-ray image pickup signal and a CT value at each position in the body is calculated. A material composition at each position is estimated from the CT value obtained. Then, a linear attenuation coefficient at each position at 511 keV is estimated from the material composition data. Using the linear attenuation coefficient data obtained, a linear attenuation coefficient of an attenuation between a pair of semiconductor devices in which a pair of γ-rays are detected is calculated according to the forward projection method. The reciprocal of the linear attenuation coefficient calculated is multiplied on the count rate of the γ-ray image pickup signal and thereby the data difference due to the attenuation in the body is corrected.

The tomography of a cross section of the examinee 35 including the affected area (e.g., the affected area of cancer) is reconstructed using the corrected count rate of the γ-ray image pickup signal at the corresponding position (step 60). The tomography reconstructed using the count rate of the γ-ray image pickup signal is called a "PET image". This processing will be explained in detail. Using the count rate of the γ-ray image pickup signal read from the storage device 28, a linear attenuation coefficient in the body of an attenuation between the semiconductor devices of a pair of the radiation detectors 4 (specified by position information of the detection point) which has detected a pair of γ-rays is calculated. Using this linear attenuation coefficient, a linear attenuation coefficient of each voxel is calculated according to the filtered back projection method. Using the linear attenuation coefficient of each voxel calculated, radiation density at each voxel is calculated. PET image data can be obtained based on this radiation density. This PET image data is stored in the storage device 28.

The PET image data is fused with the X-ray computed tomographic image data to obtain fused tomographic data including both data pieces and stored in the storage device 28 (step 61). Fusion of the PET image data and X-ray computed tomographic image data can be performed easily and accurately by aligning the central axis of the through hole section 30 in both image data pieces. That is, the PET image data and X-ray computed tomographic image data are created based on the image pickup signals output from the common radiation detector 4, and therefore alignment can be performed accurately as described above. The fused tomographic data is called from the storage device 28 and output to the display device 29 (step 29) and displayed on the display of the monitor 32. The fused tomography displayed on the monitor 32 includes an X-ray computed tomographic image, and therefore it is possible to easily check the position in the body of the examinee 7 of the affected area in the PET image. That is, since the X-ray computed tomographic image includes images of internal organs and bones, doctors can identify the position of the affected area (e.g., the affected area of cancer) from the relationship with the internal organs or bones.

An X-ray computed tomographic image requires a plurality of scan data pieces, and therefore the required amount of data can be calculated from the radiation detector 4 by moving the X-ray source 3 along the guide rail 50 using the X-ray source drive 17.

In this embodiment, each radiation detector 4 detects both X-rays passing through the body of the examinee 35 (called "penetrating X-rays") and γ-rays radiated from within the body caused by the PET radiopharmaceutical. For this reason, the conventional technologies require an image pickup apparatus for detecting penetrating X-rays and another image pickup apparatus for detecting γ-rays as image pickup apparatuses. This embodiment allows only one image pickup apparatus 2 to detect both the above-described penetrating X-rays and γ-rays, thus simplifying the configuration of the radiological imaging apparatus significantly and reducing the size of the radiological imaging apparatus. Furthermore, this embodiment makes it possible to separate an X-ray image pickup signal and γ-ray image pickup signal from the output signal of the radiation detectors 4 that detect both penetrating X-rays and γ-rays, reconstruct a first tomographic image (X-ray computed tomographic image) including internal organs and bones of the examinee using the intensity of the separated X-ray image pickup signal and reconstruct a second tomographic image (PET image) including images of the affected area of the examinee using the intensity of the separated γ-ray image pickup signal. Since the first tomographic image data and second tomographic image data are reconstructed based on the output signal of the radiation detectors 4 that detect both penetrating X-rays and γ-rays, it is possible to fuse the first tomographic image data and second tomographic image data with accurate alignment and easily obtain accurate tomographic images (fused tomographic images) of the affected area, internal organs and bones. This fused tomographic image makes it possible to exactly identify the position of the affected area based on the relationship with internal organs or bones.

Since this embodiment can obtain image pickup signals necessary to create a first tomographic image and image pickup signals necessary to create a second tomographic image from common radiation detectors 4, it is possible to shorten the time required to inspect the examinee (inspection time) significantly. In other words, this embodiment can obtain image pickup signals necessary to create a first tomographic image and image pickup signals necessary to create a second tomographic image in a short inspection time. This embodiment eliminates the need to move the examinee from an image pickup apparatus that detects penetrating X-rays to another image pickup apparatus that detects γ-rays as in the case of the conventional technology, and can thereby reduce the probability that the examinee will move. Eliminating the need to move the examinee from an image pickup apparatus that detects penetrating X-rays to another image pickup apparatus that detects γ-rays also contributes to shortening of the time of examining the examinee.

Since this embodiment includes an array of ring-shaped radiation detectors 4 placed around the through hole section 30 into which the examinee 35 is inserted, it is possible to detect X-rays passing through the examinee 35 and γ-rays radiated from the examinee 35 caused by radiopharmaceutical. This effect can also be obtained in Embodiments 2 to 12 which will be described later. Especially according to embodiments 1 to 3 and Embodiments 6 to 12, a plurality of ring-shaped radiation detector arrays is placed in the longitudinal direction of the bed 16, and therefore the detection efficiency of multiple γ-ray pairs radiated from the examinee 35 in all directions increases.

Furthermore, the time required to inspect an X-ray image pickup signal to create an X-ray computed tomographic image is shorter than the time required to obtain a γ-ray image pickup signal to create a PET image. Thus, by always irradiating the examinee with X-rays from the X-ray source 9 and obtaining an X-ray image pickup signal during an inspection time to obtain a γ-ray image pickup signal, it is possible to correct deviations of PET image data due to movements of the examinee from continuous X-ray computed tomographic images obtained based on the X-ray image pickup signal even if the examinee moves during the inspection.

The semiconductor radiation detector used as the radiation detector 4 has high energy resolution. Thus, this embodiment can easily separate the X-ray image pickup signal and γ-ray image pickup signal output from the radiation detectors 4 using the signal discriminators 19.

By the way, it is not necessary to conduct both an X-ray computed tomographic inspection and PET inspection on the examinee for all the time of inspection. There can also be times for conducting only a PET inspection or only an X-ray computed tomographic inspection according to the required amount of data.

(Embodiment 2)

A radiological imaging apparatus according to another embodiment of the present invention will be explained. Though not shown, the configuration of this embodiment uses a signal discriminator 19A shown in FIG. 8 instead of the signal discriminator 19 in the configuration in FIG. 1. The signal discriminator 19A can also be used as a substitute for the signal discriminator 19 in Embodiment 4, which will be described later. The signal discriminator 19A has a configuration with a changeover switch 31 added to the aforementioned signal discriminator 19 and the pulse height analyzer 38 replaced by a signal processor 22. The signal discriminator 19A is provided with a waveform shaping device 20, a γ-ray discriminator 21 and the signal processor 22 for calculating the intensity of X-rays. The signal processor 22 is provided with an integrator (not shown). The changeover switch 31 includes a movable terminal 32 and fixed terminals 33 and 34. Wiring 23 is connected to the movable terminal 32. The waveform shaping device 20 is connected to the fixed terminals 33 and γ-ray discriminator 21. The signal processor 22 is connected to the fixed terminal 34. The signal discriminator 19A is a signal processor, provided with a signal processor 22 which is a first signal processor and a second signal processor provided with the waveform shaping device 20 and γ-ray discriminator 21.

In the case of the signal discriminator 19 shown in FIG. 2, a γ-ray image pickup signal and X-ray image pickup signal are input to the γ-ray discriminator 21 and the pulse height analyzer 38, and therefore it is not possible to maintain the amount of each signal to a fixed value. Furthermore, it may also be preferred that the time interval of X-rays radiated from the X-ray source 9 be shorter than time window Δr of the signal discriminator to shorten the inspection time of an X-ray computed tomographic inspection. To meet this requirement, the signal discriminator 19A of this embodiment is constructed by including the changeover switch 31 so that an image pickup signal sent through the wiring 23 is transmitted to the γ-ray discriminator 21 or signal processor 22 through a changeover of the changeover switch 31. During a PET inspection, the movable terminal 32 is connected to the fixed terminal 33 to carry out a PET inspection.

A changeover operation for connecting the fixed terminal 33 or fixed terminal 34 of the changeover switch 31 is performed based on a control signal which is the output of the drive controller 17. The drive controller 17 controls movements of the X-ray source apparatus 8 as described above, but at the same time selects the radiation detector 4 which is 180° opposite to the X-ray source 9 and connects the movable terminal 32 of the changeover switch 31 of the signal discriminator 19A connected to the selected radiation detector 4 to the fixed terminal 34.

The way of selection of the above-described radiation detector 4 (located 180° opposite to the X-ray source 3) will be explained. The motor in the X-ray source drive 10 is coupled with an encoder (not shown). The drive controller 17 is fed a detection signal of the encoder and determines the position of the X-ray source 9 on the guide rail 12 and selects the radiation detector 4 located 180° opposite to the X-ray source 9 using the data of the position of each radiation detector 4 stored. Since the X-rays radiated from the X-ray source 9 have a certain breadth in the circumferential direction of the guide rail 12, there is a plurality of the radiation detectors 4 that detect X-rays passing through the body of the examinee 35 in the circumferential direction in addition to the selected radiation detector 4. The drive controller 17 also selects the plurality of the radiation detectors 4. Therefore, the drive controller 17 also connects the movable terminals 32 of a plurality of changeover switches 31 connected to the radiation detectors 4 to the fixed terminal 34. When the drive controller 17 selects another radiation detector 4 because of a movement of the X-ray source 9, the movable terminal 32 connected to the newly selected radiation detector 4 is connected to the fixed terminal 34. The movable terminal 32 connected to the deselected radiation detector 4 is connected to the fixed terminal 33 by the drive controller 17.

A γ-ray image pickup signal output from the radiation detector 4 is input to the γ-ray discriminator 21 via the waveform shaping device 20 with the movable terminal 32 connected to the fixed terminal 33 and processed in the same way as for the above-described radiological imaging apparatus 1. A pulse signal output from the γ-ray discriminator 21 is input to the coincidence detector 26. The count rate of the γ-ray image pickup signal output from the coincidence detector 26 is input to the computer 27, processed by the radiological imaging apparatus 1A and PET image data is obtained in this way. In this embodiment, as will be described later, no X-rays are entered to the radiation detector 4 while the movable terminal 32 is connected to the fixed terminal 33, and therefore only the γ-ray image pickup signal is input to the waveform shaping device 20 and γ-ray discriminator 21. The γ-ray discriminator 21 deletes low energy γ-ray signals which will adversely affect creation of PET image data by the first filter. Thus, it is possible to obtain PET image data with high accuracy.

Then, processing of an X-ray image pickup signal output from the radiation detector 4 will be explained using FIGS. 9A–9D. Since the time interval of X-rays radiated from the X-ray source 9 is smaller than time window Δτ of the signal discriminator 19A, a plurality of X-rays is entered to the radiation detector 4 for a time period of Δτ. On the other hand, in the case of γ-rays generated caused by PET radiopharmaceutical, if a plurality of γ-ray pairs is generated for a time period of Δτ, it is unknown between which radiation detectors 4 the γ-rays are generated. For this reason, the system is constructed so that only a maximum of one γ-ray pair on average is generated in the body of the examinee for a time period of Δτ. This is possible by adjusting the amount of PET radiopharmaceutical to be administered to the examinee 35 to an amount so that only a maximum of one γ-ray pair on average is generated in the body for a time period of Δτ. Since the number of radiation detectors 4 amounts to several thousands or tens of thousands for a general PET apparatus, the probability that a plurality of γ-rays will enter the same radiation detector for a time period of 10Δτ, etc. is nearly 0. Thus, suppose, for example, X-rays are radiated from the X-ray source 9 for an inspection time of 10Δτ and γ-rays are entered to the radiation detector 4 once in that period (FIG. 9B). Then, the X-ray image pickup signal produced by the X-rays passing through the body and the γ-ray image pickup signal produced by γ-rays are as shown in FIGS. 9D and 9C. As a result, the image pickup signal output from the radiation detector 4 appears as shown in FIG. 9B. Therefore, the intensity of the X-ray image pickup signal is obtained by averaging signals obtained by removing, for example, the largest signal from the output signal of the radiation detector 4.

While the movable terminal 32 is connected to the fixed terminal 34, the X-ray image pickup signal detected by the radiation detector 4 and an extremely small number of γ-ray image pickup signals are input to the signal processor 22 and these image pickup signals are integrated by an integrator. This integration of image pickup signals is performed while the movable terminal 32 is connected to the fixed terminal 34, and the integration is completed when the movable terminal 32 is connected to the fixed terminal 33.

The signal processor 22 inputs the integrated value of X-ray image pickup signals, that is, information on the intensity of the X-ray image pickup signal to the computer 27. In this embodiment, "Input count rate of X-ray image pickup signal" in step 54 in FIG. 5 corresponds to "Input intensity of X-ray image pickup signal" and "Store count rate of X-ray image pickup signal" in step 55 corresponds to "Store intensity of X-ray image pickup signal" and the processing in step 56 is not performed. The processing in step 55 is followed by the processing in step 57. The calculation processing in step 57 subtracts the integrated value of the γ-ray image pickup signal (integrated value of predetermined number (1 or 2) of the γ-ray image pickup signal) from the intensity of the X-ray image pickup signal entered and averages the result by the time during which the movable terminal 32 is connected to the fixed terminal 34 and thereby calculates average intensity of the X-ray image pickup signal. Based on this average intensity, an attenuation rate at each voxel is calculated and X-ray computed tomographic image data is obtained in step 58.

Using the signal discriminator 19A improves the maintainability of a fixed amount of γ-ray image pickup signal and X-ray image pickup signal. The radiological imaging apparatus of the present invention using the signal discriminator 19A instead of the signal discriminator 19 also produces the effect described in Embodiment 1. Though this embodiment does not perform processing of separating the X-ray image pickup signal and γ-ray image pickup signal from the output signal of the radiation detector 4 as in the case of Embodiment 1, this embodiment can create X-ray computed tomographic image data based on the X-ray image pickup signal output from the radiation detector 4, and can thereby obtain PET image data based on the γ-ray image pickup signal.

(Embodiment 3)

Figure 10:
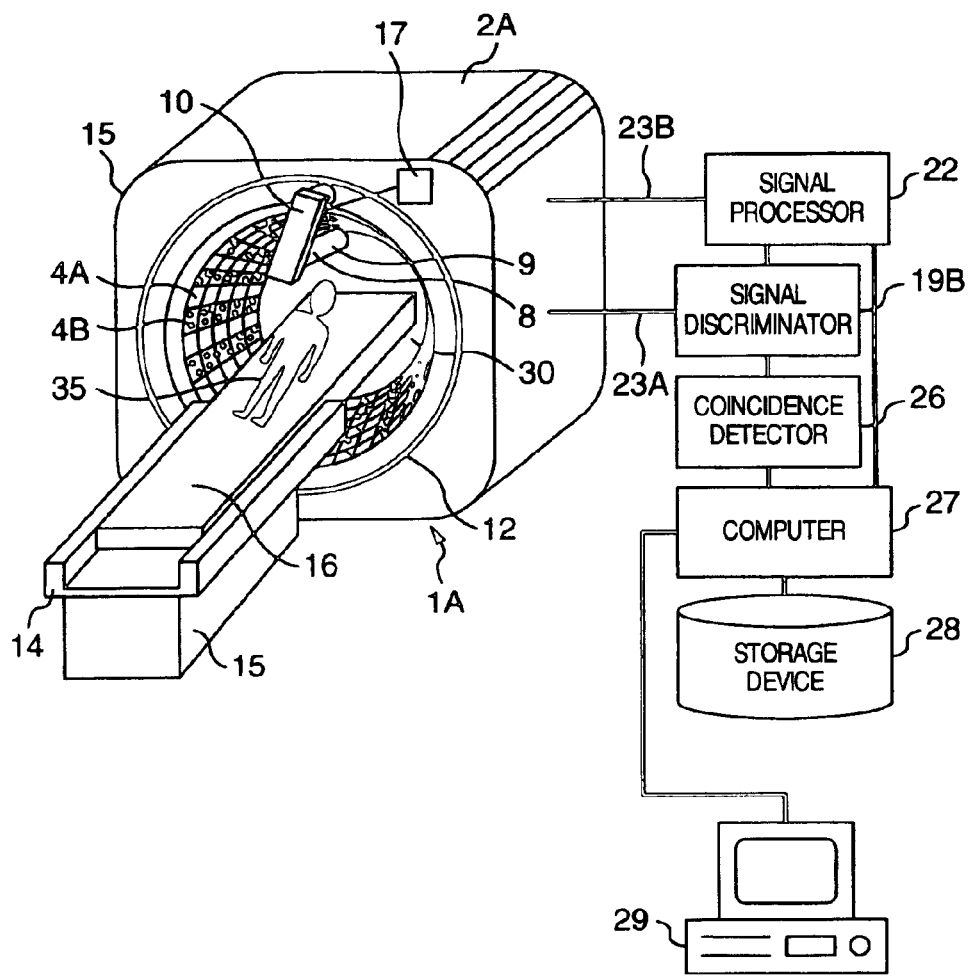
FIG. 10 is a perspective view of a radiological imaging apparatus which is another embodiment of the present invention.
Figure 11:
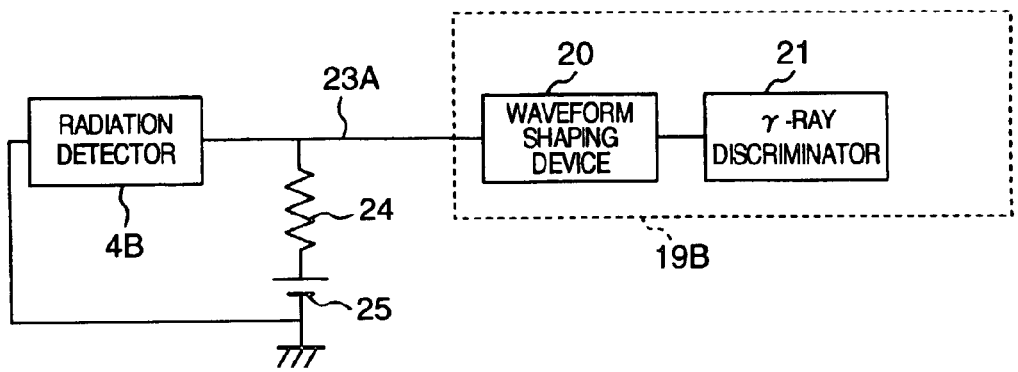
FIG. 11 is a detailed block diagram of the signal discriminator in FIG. 10.

A radiological imaging apparatus according to another embodiment of the present invention will be explained using FIG. 10. This embodiment shows an example of conducting X-ray computed tomographic inspection and PET inspection using one image pickup apparatus 2A. The radiological imaging apparatus 1A of this embodiment is provided with a radiation detector 4A connected to a signal processor 22 via wiring 23B and a radiation detector 4B connected to a signal discriminator 19B via wiring 23A. The radiation detector 4A and radiation detector 4B are semiconductor radiation detectors as in the case of the radiation detector 4. The radiation detector 4A and radiation detector 4B are placed alternately in the circumferential direction of the through hole section 30 of the image pickup apparatus 2A. The radiation detector 4A and radiation detector 4B need not always be placed alternately, but the ratio of their arrangement can be changed if necessary. The signal discriminator 19B is a signal processor.

The signal discriminator 19B is provided with a waveform shaping device 20 and γ-ray discriminator 21 connected in series. The waveform shaping device 20 is connected to the wiring 23A.

The radiation detector 4A and radiation detector 4B output both X-ray image pickup signal and γ-ray image pickup signal as in the case of the radiation detector 4 in the embodiment in FIG. 1. The signal processor 22 connected to the radiation detector 4A outputs the intensity of an X-ray image pickup signal as in the case of the signal processor 22 of the above-described signal discriminator 19A. The waveform shaping device 20 and γ-ray discriminator 21 to which the output of the radiation detector 4B is input perform the same processing as that of the signal discriminator 19. The γ-ray discriminator 21 generates pulse signals based on a γ-ray image pickup signal.

The processing by the computer 27 of this embodiment is the same as that described in Embodiment 2. Finally, fused tomographic image data combining the X-ray computed tomographic image data and PET image data is obtained. This embodiment can obtain the effect described in Embodiment 2. In order to compensate for a reduction of image quality of a PET image and X-ray computed tomographic image due to the existence of positions where no γ-rays are detected (position where the radiation detector 4A is placed) and positions where no X-rays are detected (position where the radiation detector 4B is placed) by alternately placing the radiation detector 4A and radiation detector 4B, the radiation detector 4A and radiation detector 4B are rotated in the circumferential direction of the through hole section 30, for example, using a motor. This makes it possible to detect X-rays and γ-rays meticulously in the circumferential direction. This can prevent image quality of a PET image or X-ray computed tomographic image from deteriorating.

(Embodiment 4)

Figure 12:
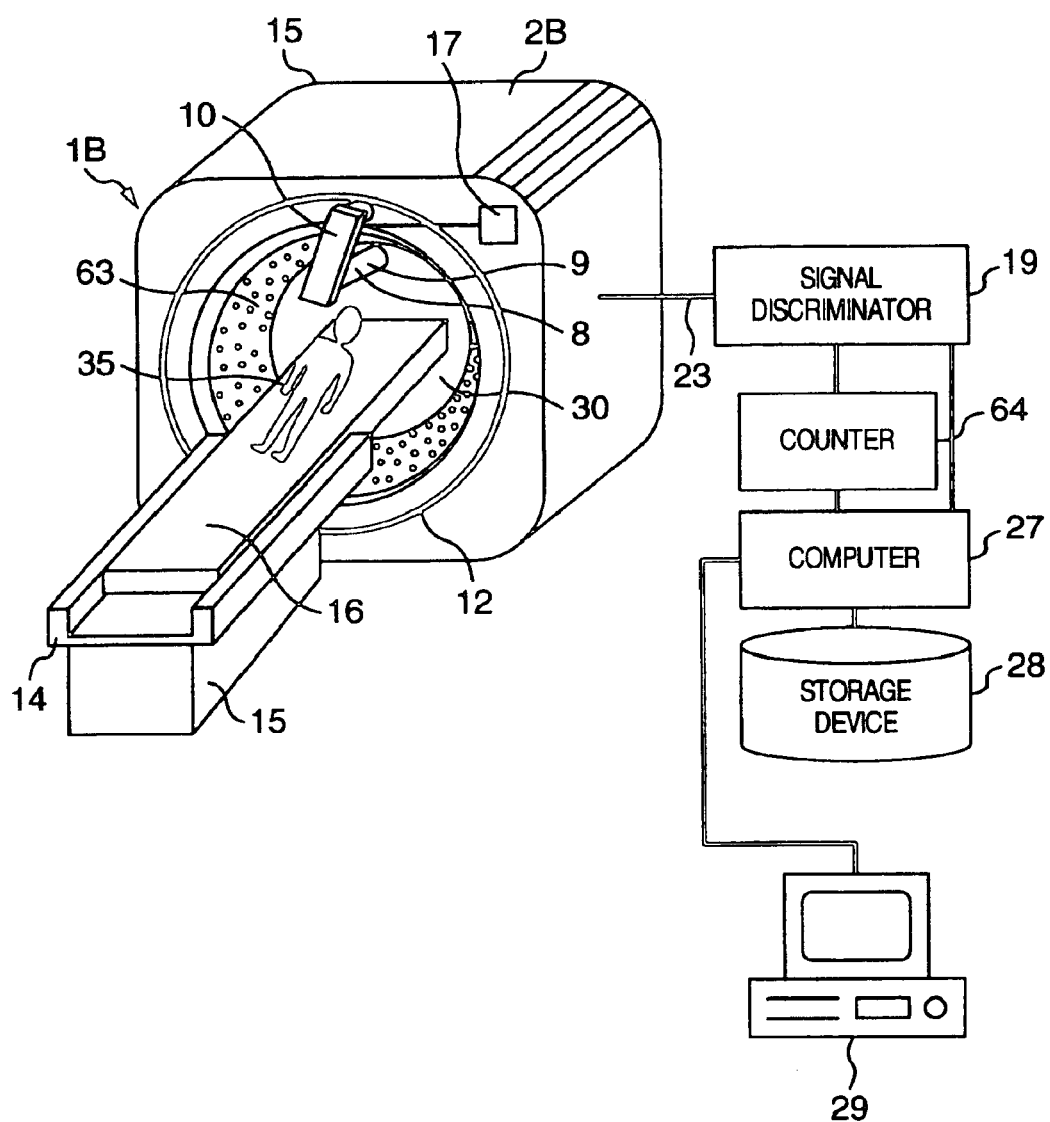
FIG. 12 is a perspective view of a radiological imaging apparatus which is another embodiment of the present invention.

A radiological imaging apparatus 1B which is another embodiment of the present invention will be explained based on FIG. 12. The radiological imaging apparatus 1B has the functions of an X-ray computed tomographic apparatus and SPECT apparatus. An image pickup apparatus 2B of the radiological imaging apparatus 1B includes a collimator 63 inside the radiation detector ring structure in the image pickup apparatus 2 of the radiological imaging apparatus 1. The remaining configuration of the radiological imaging apparatus 1B is the same as that of the radiological imaging apparatus 1. A counter 5A is connected to the respective γ-ray discriminators 42 of the signal discriminators 4. A counter 64 may also be provided for several γ-ray discriminators 21. A collimator 63 is provided for each radiation detector 4 (not shown in FIG. 12) in such a way as to face each other and has a through hole through which X-rays and γ-rays pass. This embodiment shows an example of performing an X-ray computed tomographic inspection and SPECT inspection (act of detecting γ-rays radiated from within the body of the examinee 35 caused by SPECT radiopharmaceutical using a radiation detector) using one image pickup apparatus 2B.

During a SPECT inspection, the examinee 35 is administered with SPECT radiopharmaceutical including the above-described single photon radiateters and laid down on the bed 16 and single γ-rays generated in the body of the examinee 35 caused by the SPECT radiopharmaceutical are detected by the radiation detectors 4. To detect γ-rays entering from a specific angle, the collimator 63 is placed as described above. For example, the collimator 63 allows γ-rays perpendicular to the radiation detector 4 to enter the radiation detectors 4.

When X-rays passing through the body of the examinee 35 are detected by the radiation detectors 4, X-rays entering in a direction diagonal to the radiation detectors 4 are also necessary. If such X-rays are blocked by the collimator 63, it is not possible to perform an X-ray computed tomographic inspection. Thus, this embodiment uses the X-ray source 9 to generate high energy X rays, irradiates these X rays onto the examinee 35 to detect the X-rays that have passed through the body using the radiation detectors 4. The X-ray source 9 in this embodiment radiates X-rays having higher energy than the X-ray source 9 used in the embodiment in FIG. 1.

The energy of γ-rays caused by SPECT radiopharmaceutical is lower than the energy of γ-rays caused by PET radiopharmaceutical. The energy of γ-rays caused by SPECT radiopharmaceutical ranges from approximately 80 eV to 130 keV, for example. In this case, the collimator 63 is constructed so that γ-rays having energy equal to or lower than approximately 80 eV do not pass through other than the through hole.

The X-rays radiated from the X-ray source 9 are prevented from having the same energy as that of γ-rays produced by the SPECT radiopharmaceutical and further adjusted to have energy capable of penetrating parts other than the through hole of the collimator 63. This makes it possible to conduct an X-ray computed tomographic inspection with the collimator 63 mounted. Suppose a case where the energy of X-rays is 300 keV, the energy of γ-rays is 100 keV and tungsten is used as the material of the collimator 63. While the linear attenuation coefficient of tungsten photons with 300 keV is approximately 6.0 cm$^{-1}$, the linear attenuation coefficient of photons with 100 keV is approximately 83 cm$^{-1}$. For this reason, when an X-ray and γ-ray penetrate the collimator 10 by 0.5 mm, while the X-ray penetrates 75%, the γ-ray only penetrates 2%. As a result, the radiation detector 4 also outputs an output signal for an X-ray that enters the radiation detector 4 diagonally, but outputs no output signal for a γ-ray that is blocked by the collimator 63 and enters diagonally.

In this embodiment, each radiation detector 4 detects both X-rays radiated from the X-ray source 9 and passing through the body of the examinee 35 and γ-rays radiated from the affected area caused by SPECT radiopharmaceutical and outputs an output signal (an image pickup signal) including X-ray image pickup signal and a detection signal of γ-rays (γ-ray image pickup signal). The signal discriminator 19 separates the X-ray image pickup signal and γ-ray image pickup signal from the image pickup signal. In this embodiment, the γ-ray discriminator 21 outputs a pulse signal when an image pickup signal (γ-ray image pickup signal) having energy equal to or lower than a first energy set value (e.g., 120 keV) is input. The counter 64 counts the pulse signal and calculates a count rate for the γ-ray image pickup signal. The pulse height analyzer 38 outputs a count rate of an image pickup signal (X-ray image pickup signal) having energy ranging from a second energy set value (e.g., 290 keV) to a third energy set value (310 keV). The count rates of the γ-ray image pickup signal and the X-ray image pickup signal are input to the computer 27 and stored in the storage device 28. The computer 27 executes processing based on the procedure shown in FIG. 5 using those count rates. Of steps 54 to 62 executed in this embodiment, only the processing of steps different from the processing of steps executed in Embodiment in FIG. 1 will be explained below. Unlike the correction executed in step 56 of the embodiment shown in FIG. 1, the correction of a count rate of an X-ray image pickup signal in step 56 in this embodiment is executed using a linear attenuation coefficient of the collimator 63. This correction will be explained in detail below.

Since the count rate of the X-ray image pickup signal obtained includes the count rate of the X-rays that have passed through the collimator 63, this count rate needs to be corrected using the linear attenuation coefficient of the collimator 63. For example, in the case where the collimator 63 is made of tungsten and the X-ray penetrates the collimator 63 by 1 mm, the count becomes approximately 0.55 times based on the above-described linear attenuation coefficient. Thus, it is possible to correct the count rate by multiplying the count rate of the X-ray image pickup signal stored in the storage device 28 by its reciprocal.

In step 60 of this embodiment, it is possible to perform processing of reconstructing a SPECT image using a filtered back projection method. The SPECT image refers to a tomographic image of a cross section of the examinee 35 reconstructed using the count rate of the γ-ray image pickup signal obtained in this embodiment. In step 61 of this embodiment, the X-ray computed tomographic image data is fused with the SPECT image data accurately by matching the central axis of the through hole section 30 of the image pickup apparatus corresponding to the X-ray computed tomographic image data obtained in step 58 with that corresponding to the SPECT image data obtained in step 60. The fused tomographic image data obtained is stored in the storage device 28.

This embodiment obtains fused tomographic image data by combining the X-ray computed tomographic image data and the SPECT image data obtained based on both of the above-described output signals from the radiation detector 4 and can attain the effects produced in the embodiment in FIG. 1. The "PET image" in the description of the effect of the embodiment in FIG. 1 corresponds to the "SPECT image" in this embodiment.

Both X-ray computed tomographic inspection and SPECT inspection need not be performed during an entire period of inspection on the examinee. There can also be times during which only a SPECT inspection is conducted or only X-ray computed tomographic inspection is conducted depending on the required amount of data.

In each image pickup apparatus used in Embodiment 2, Embodiment 3 and Embodiment 6, it is also possible to place the collimator 63 on the center side of the through hole section 30 of each radiation detector as in the case of this embodiment. Each image pickup apparatus having such a collimator 63 can be used for a SPECT inspection.

(Embodiment 5)

A radiological imaging apparatus 1C according to another embodiment of the present invention will be explained using FIG. 13 and FIG. 14. Like the above-described radiological imaging apparatus 1B, the radiological imaging apparatus 1C has the functions of an X-ray computed tomographic apparatus and SPECT apparatus. The radiological imaging apparatus 1C is different from the radiological imaging apparatus 1B in that the image pickup apparatus 2B of the radiological imaging apparatus 1B is replaced by the image pickup apparatus 2C. The remaining configuration of the radiological imaging apparatus 1C except the image pickup apparatus 2C is the same as that of the radiological imaging apparatus 1B. The image pickup apparatus 2C has a configuration capable of moving the collimator 63 and X-ray source 9 in the axial direction of the through hole section 30 and this configuration does not exist in the image pickup apparatus 2B. The remaining configuration of the image pickup apparatus 2C is the same as that of the image pickup apparatus 2B. This embodiment shows an example where an X-ray computed tomographic inspection and a SPECT inspection are carried out using one image pickup apparatus 2C.

The collimator 63 is mounted on a plurality of linear horizontal guide rails (not shown) extending in the axial direction of the through hole section 30 installed inside the casing 15 in such a way as to be movable in the horizontal direction. The collimator drive that drives the collimator 63 in the horizontal direction includes a motor mounted in a collimator storage area 65 inside the casing 15, a pinion connected to the rotational axis of this motor and a rack provided on the circumference of the collimator 63, all of which are not shown. The rack extends in the axial direction of the through hole section 30 on the circumference of the collimator 63 in such a way as to avoid the through holes of the collimator 63. The pinion engages with the rack. The collimator 63 provided with the rack moves in the axial direction of the through hole section 30 by the pinion that rotates by a rotational force of the motor. The X-ray source drive 10 includes another drive mechanism (second drive mechanism, not shown) to move the X-ray source 9 in the axial direction of the through hole section 30 in addition to the drive mechanism (first drive mechanism) that moves the above-described X-ray source apparatus 8 along the guide rail 12. This second drive mechanism includes a second power transmission mechanism connected to the above-described motor of the X-ray source drive 10 via a second clutch and a pinion connected to the second power transmission mechanism engaging with the rack (extending in the axial direction of the through hole section 30) provided for the X-ray source 9. This embodiment connects the power transmission mechanism of the first drive mechanism (first power transmission mechanism) and the above-described motor through the first clutch.

Figure 13:
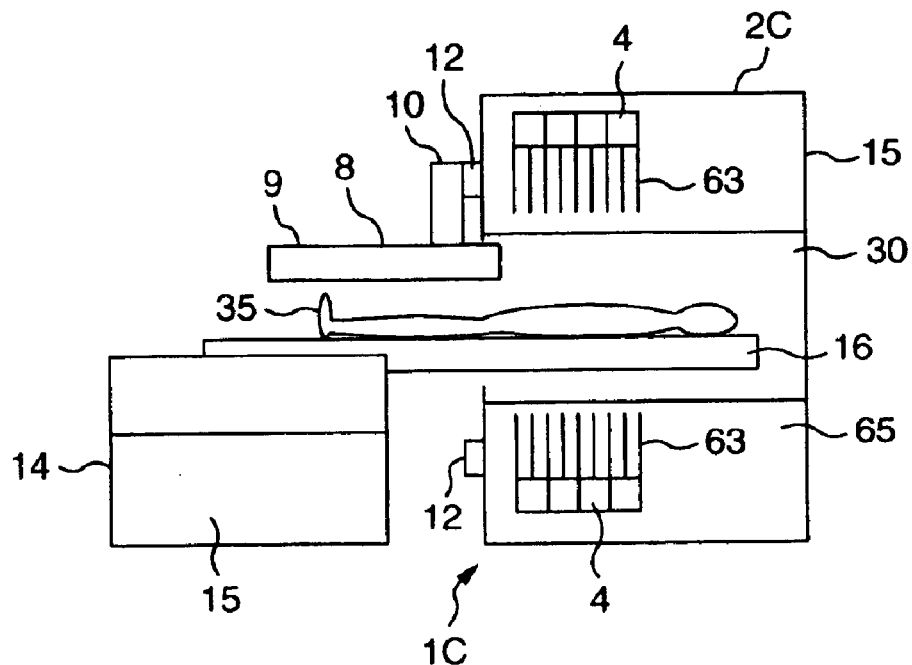
FIG. 13 is a longitudinal sectional view of a radiological imaging apparatus which is another embodiment of the present invention.
Figure 14:
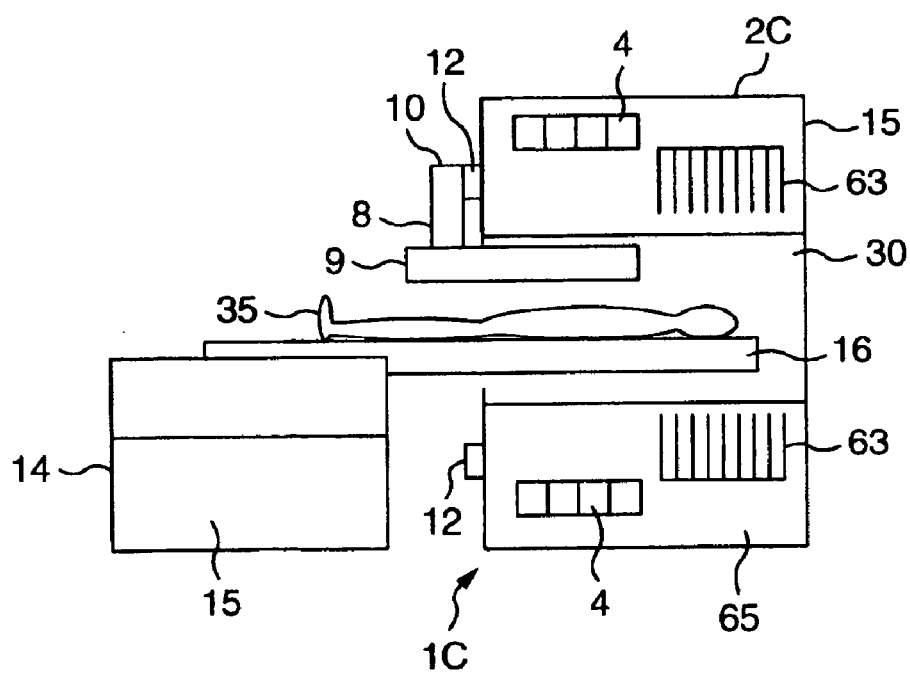
FIG. 14 illustrates a collimator in the embodiment shown in FIG. 12 shifted from a position of the radiation detector.

The collimator 63 in this embodiment is moved to the front of the radiation detector 4 by the collimator drive as shown in FIG. 13 before a SPECT inspection is started. Furthermore, before a SPECT inspection is started, the collimator drive releases the connection between the motor and the first power transmission mechanism by the first clutch and connects the motor and the second power transmission mechanism by the second clutch and drives the motor to move the X-ray source 9 from the front of the radiation detector 4 to the outside of the through hole section 30. A SPECT inspection is performed in this condition. The collimator 63 is housed in the collimator storage area 65 by the collimator drive before an X-ray computed tomographic inspection is started as shown in FIG. 14. The X-ray source 9 is inserted into the through hole section 30 by driving the motor with the motor and the second power transmission mechanism connected by the second clutch before the X-ray computed tomographic inspection is started and positioned in front of the radiation detector 4 as shown in FIG. 14.

The examinee 35 administered with SPECT radiopharmaceutical is laid down on the bed 16. During a SPECT inspection, it is necessary to identify the direction of γ-rays entering the radiation detector 4 using the collimator 63 as described above. Thus, the SPECT inspection is performed in the condition shown in FIG. 13. During the SPECT inspection, only a γ-ray image pickup signal is output from the radiation detector 4 and pulse signals are output from the γ-ray discriminator 21 of the signal discriminator 19 to the γ-ray image pickup signal. Pulse signals are counted by the counter 64 and input to the computer 27 (not shown) as the count rate of the γ-ray image pickup signal.

During an X-ray computed tomographic inspection, the X-ray source drive 10 connects the motor and the first power transmission mechanism by the first clutch (the second clutch is detached) and drives the motor to move the X-ray source apparatus 8 along the guide rails 12. X-rays passing through the body of the examinee 35 are detected by the radiation detector 4. The radiation detector 4 only outputs an X-ray image pickup signal and the pulse height analyzer 38 of the signal discriminator 19 outputs the count rate of the X-ray image pickup signal. This count rate is also input to the computer 27. The computer 27 performs processing similar to that of the computer 27 of the radiological imaging apparatus 1B and obtains fused tomographic image data by combining the SPECT image data and the X-ray computed tomographic image data. This fused tomographic image data is displayed on the display device 29 (not shown).

In this embodiment, a single image pickup apparatus 2C can detect both the above-described penetrating X-rays and γ-rays, not requiring two radiation detectors for two image pickup apparatuses and simplifying the configuration of the radiological imaging apparatus significantly.

This embodiment can reconstruct a first tomographic image (X-ray computed tomographic image) of the examinee described in Embodiment 1 using the intensity of X-ray image pickup signal separated from the output signal of the radiation detector 4 and reconstruct a second tomographic image (SPECT image) including images of the affected area of the examinee using the intensity of the separated γ-ray image pickup signal. This embodiment can make a fusion accurately and easily obtain exact tomographic images including images of affected areas, internal organs and bones as in the case of Embodiment 1. This fused tomographic image makes it possible to accurately identify the positions of affected areas in relation with internal organs and bones.

For the same reason as that described in Embodiment 1, this embodiment contributes to the shortening of a time for inspecting the examinee. The inspection time is further reduced by setting the moving direction of the bed 16 during a SPECT inspection opposite to the moving direction of the bed 16 during an X-ray computed tomographic inspection. For example, an X-ray computed tomographic inspection is performed while moving the bed 16 in the direction in which the bed 16 is inserted into the through hole section 30 and just after the X-ray computed tomographic inspection is completed, a SPECT inspection is performed while moving the bed 16 in the direction in which the bed 16 is pulled out of the through hole section 30. This case shortens the inspection time compared to the SPECT inspection conducted with the bed 16 pulled out of the through hole section 30 after the X-ray computed tomographic inspection is completed and reinserted into the through hole section 30.

The X-ray source 9 of this embodiment may also be an X-ray source that radiates X-rays with lower energy than the X-ray source 9 of the radiological imaging apparatus 1B, in which case the system becomes more compact. Furthermore, this embodiment can use low energy X-rays, and can thereby reduce burdens on the examinee. However, in the case where the energy of X-rays is reduced down to the level of the energy of γ-rays radiated from within the body caused by SPECT radiopharmaceutical, the signal discriminator 19 cannot discriminate the energy of an X-ray image pickup signal from the energy of a γ-ray image pickup signal. For this reason, for example, if SPECT radiopharmaceutical producing 80 keV γ-rays is used, it is necessary to use 100 keV X-rays, for example.

The radiation detector 4 detects γ-rays radiated from within the body also during an X-ray computed tomographic inspection with the collimator 63 housed in the collimator storage area 65. At this time, no angle information is obtained with respect to γ-rays entered to the radiation detector 4. If SPECT image data can be obtained based on this γ-ray detection signal (γ-ray image pickup signal), the collimator 63 is unnecessary even if the X-ray source radiates low energy X-rays, which makes it possible to reduce the size of the through hole section 30 of the image pickup apparatus 1C in the axial direction. This leads to a reduction of the size of the image pickup apparatus 2C. Two methods are available to realize this. A first method is to estimate the count of γ-rays entered to the radiation detector 4 while the collimator 63 is housed in the collimator storage area 65 supposing a specific distribution condition. A second method is to use the time for detecting γ-rays of the radiation detector 4 having the longest time period during which the collimator 63 is not located on the front as a reference time and adjust the count rate of γ-rays detected by another radiation detector 4 to the count rate corresponding to the reference time. Using the first or second method, weights of count rates obtained using a γ-ray image pickup signal which is the output of each radiation detector 4 are equalized and SPECT image data is calculated using, for example, the filtered back projection method.

(Embodiment 6)

Figure 15:
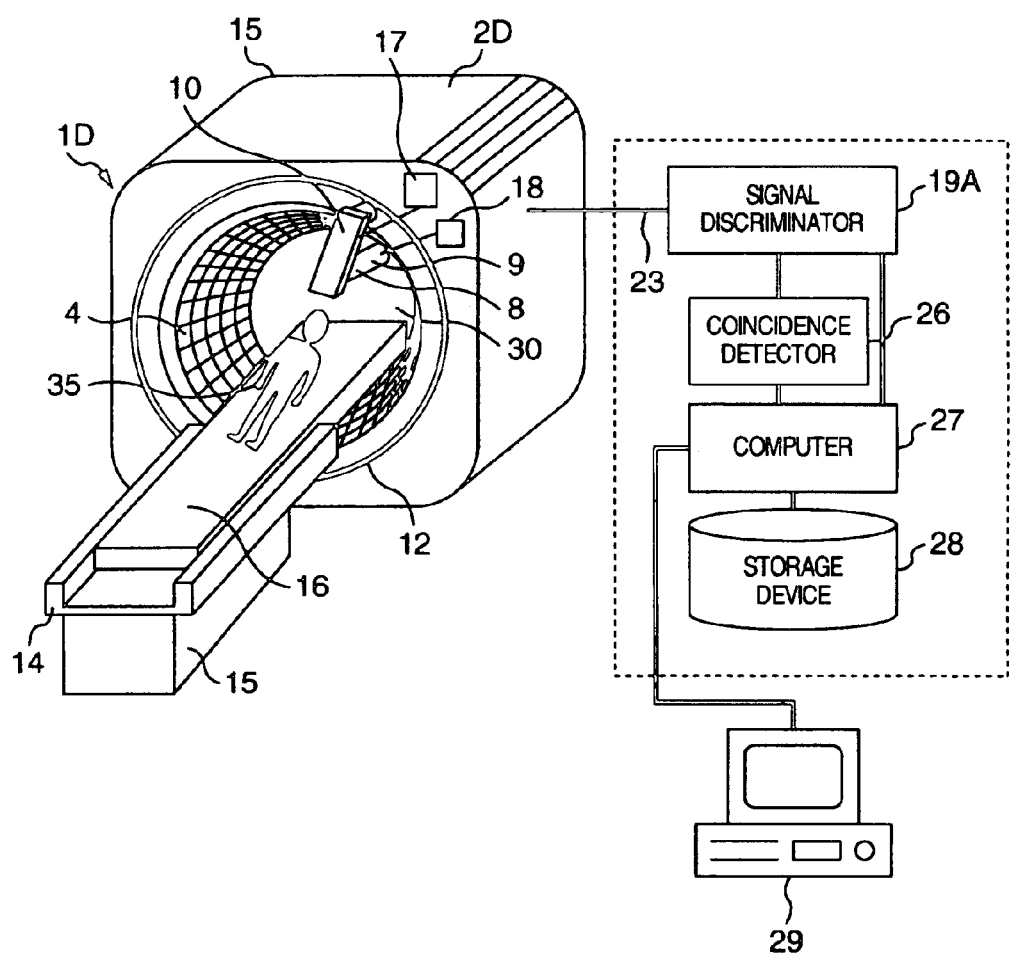
FIG. 15 is a perspective view of a radiological imaging apparatus which is another embodiment of the present invention.

A radiological imaging apparatus 1D according to another embodiment of the present invention will be explained using FIG. 15 below. The radiological imaging apparatus 1D has a configuration with an X-ray source controller 18 added to the configuration of the radiological imaging apparatus 1 and the signal discriminator 19 of the radiological imaging apparatus 1 replaced by a signal discriminator 19A shown in FIG. 8. The image pickup apparatus 2D has a configuration with the X-ray source controller 18 added to the image pickup apparatus 2. The remaining configuration of the radiological imaging apparatus 1D is the same as that of the radiological imaging apparatus 1. This embodiment shows an example where an X-ray computed tomographic inspection and a PET inspection are carried out using one image pickup apparatus 2D.

Before explaining specific inspections in this embodiment, the principles of radiation detection in this embodiment will be explained first. This embodiment is based on the following considerations by the present inventor et al. X-ray computed tomographic image data is created based on the intensity of X-rays detected by a radiation detector by irradiating X-rays radiated from an X-ray source in a specific direction for a predetermined time and repeating (scanning) detection of X-rays passing through the body with the radiation detector. To obtain accurate X-ray computed tomographic image data, it is preferable that no γ-rays radiated from within the body of the examinee enter the radiation detector detecting X-rays in an X-ray computed tomographic inspection. For this purpose, based on the new knowledge of the present inventor et al. that "in one radiation detector influences of γ-rays are negligible if the time of irradiation with X-rays onto the examinee is shortened according to the rate of incidence of γ-rays", this embodiment intends to shorten the time of irradiation onto the examinee with X-rays. To determine the time T of irradiation with X-rays, the rate of incidence of γ-rays into one radiation detector is considered first. Suppose radioactivity in the body based on PET radiopharmaceutical administered to the examinee in a PET inspection is N (Bq), the rate of generated γ-ray penetration through the body is A, the rate of incidence calculated from a solid angle of one radiation detector is B and the sensitivity of the radiation detector is C. The rate of γ-rays α (rays/sec) detected by one radiation detector is given by Expression (1).

$$\alpha = 2NABC \qquad (1)$$

In Expression (1), the coefficient "2" means that a pair (2 rays) of γ-rays are radiated when one positron is annihilated. A probability W that γ-rays will be detected by one radiation detector for irradiation time T is given by Expression (2).

$$W = 1 - \exp(-T\alpha) \qquad (2)$$

By determining the irradiation time T in such a way that the value of W in Expression (2) is reduced, influences of γ-rays entering one radiation detector becomes as small as negligible during an X-ray computed tomographic inspection.

An example of X-ray irradiation time T will be explained below. A specific X-ray irradiation time T is calculated based on Expressions (1) and (2). The intensity of radiation in the body caused by PET radiopharmaceutical to be administered to the examinee in a PET inspection is on the order of a maximum of 360 MBq (N=360 MBq) and the penetration rate A of γ-rays through the body is on the order of 0.6 (A=0.6) if the body of the examinee is supposed to be water having a radius of 15 cm. For example, if radiation detectors of 5 mm per side are arranged in a ring form of 50 cm radius, the rate of incidence B calculated from the solid angle of one radiation detector is $8 \times 10^{-6}$ (B=$8 \times 10^{-6}$). Furthermore, the detection sensitivity C of the radiation detector is on the order of a maximum of 0.6 (C=0.6) when a semiconductor radiation detector is used. From these values, the γ-ray detection rate α of one radiation detector is on the order of 2000 (rays/sec). Suppose X-ray irradiation time T is 1 μsec, for example. The probability W that one radiation detector will detect γ-rays during X-ray detection is 0.003. For this reason, γ-rays are almost negligible. In the case where radioactivity doses into the body are 360 MBq or less, if X-ray irradiation time is 1 μsec or less, W<0.003, that is, the γ-ray detection probability becomes 0.3% or less, which is negligible.

The X-ray source controller 18 controls the time of X-ray emission from the X-ray source 9. The X-ray source 9 includes an X-ray tube (not shown). This X-ray tube is provided with an anode, a cathode, a current source for the cathode and a voltage source for applying a voltage between the anode and cathode inside the external cylinder. The cathode consists of a tungsten filament. Electrons are emitted from the filament when current flows from the current source to the cathode. These electrons are accelerated by a voltage (several hundred kV) applied from the voltage source to between the cathode and the anode and collide with the anode (W, Mo, etc.) which is the target. Collision of electrons with the anode produces X-rays of 80 keV. These X-rays are radiated from the X-ray source 3 and irradiated onto the examinee 35 on the bed 16. The examinee 35 is administered with PET radiopharmaceutical so that the radioactivity doses in the body amount to 360 MBq.

When a drive start signal is output from the drive controller 9, the X-ray source drive 10 moves along the guide rails 12 as described above and the X-ray source 9 also moves together. The X-ray source 9 is moved along the guide rails 12 by the X-ray source drive 10 at a predetermined speed. The X-ray source controller 18 closes the switch (hereinafter referred to as "X-ray source switch", not shown) provided between the anode (or cathode) of the X-ray tube and a voltage supply during a first set time and opens during a second set time and repeats this switching control. A voltage is applied between the anode and cathode during the first set time and no voltage is applied during the second set time. This control allows a pulse-like X-rays to be radiated from the X-ray tube. The first set time is irradiation time T (e.g., 1 μsec). The second set time is a time To during which the X-ray source 9 moves between one radiation detector 4 and another radiation detector adjacent thereto and is determined by the moving speed of the X-ray source 9 in the circumferential direction of the guide rails 12. The first and second set times are stored in the X-ray source controller 18.

Detection of X-rays and signal processing of detected X-rays in an X-ray computed tomographic inspection according to this embodiment will be explained. When an X-ray computed tomographic inspection is started, a drive start signal is output from the drive controller 17 and the X-ray source 9 moves along the guide rails 12 as described above. The drive start signal is input to the X-ray source controller 18. The X-ray source controller 18 outputs an X-ray generation start signal to the X-ray source 9 or more specifically to the X-ray tube based on the input of the drive start signal. The X-ray source switch is closed by this X-ray generation start signal. A voltage is applied between the anode and the cathode and X-rays are generated. The X-rays radiated from the X-ray source 9 are irradiated onto the examinee 35 in the form of fan beams, pass through the examinee 35 and enter a plurality of radiation detectors 4 centered on the radiation detector 4 located at 180° from the X-ray source 9 with the center of the through hole section 30 as the base point also in the circumferential direction of the through hole section 30. The X-ray source controller 18 closes the X-ray switch for the first set time, that is, for 1 μsec and opens the X-ray switch for the next second set time. As the X-ray source 9 moves in the circumferential direction, the X-ray switch repeats opening/closing at the above-described time intervals. X-rays radiated while the X-ray source switch is closed enter each of the above-described radiation detectors 4 facing the above-described X-ray source 9.

As described in Embodiment 2, an output signal from each radiation detector 4 which X-rays enter is input to the signal processor 22 because the movable terminal 32 of the changeover switch 31 is connected to the fixed terminal 34 under the control of the drive controller 17. The signal processor 22 inputs information on the intensity of X-ray image pickup signals to the computer 27. 511 keV γ-rays caused by PET radiopharmaceutical are radiated from the examinee 35 and these γ-rays enter the radiation detector 4. The probability of detection of γ-rays by the radiation detector 4 to which X-rays enter is as small as negligible as described above. The radiation detectors 4 other than the radiation detector 4 which X-rays are entering detect γ-rays and output a γ-ray image pickup signal. Since the movable terminal 32 connected to these radiation detectors 4 is connected to the fixed terminal 33, the γ-ray image pickup signal is input to the waveform shaping device 20 and γ-ray discriminator 21. A pulse signal corresponding to a γ-ray image pickup signal equal to or greater than the first energy set value output from the γ-ray discriminator 21 is counted by the coincidence detector 26. The count rate of the γ-ray image pickup signal obtained is input to the computer 27. The processing performed by the computer 27 is the same as that explained in Embodiment 2. However, of the processing in step 57 executed in Embodiment 2, this embodiment does not execute an operation of subtracting an integrated value of the γ-ray image pickup signal. Fused tomographic image data is obtained through processing by the computer 27.

This embodiment can attain the effects described in Embodiment 2. In this embodiment, the number of γ-ray image pickup signals input to the signal processor 22 is reduced significantly compared to Embodiment 2. For this reason, it is possible to obtain precise X-ray computed tomographic image data based on the X-ray image pickup signals. When the finally obtained fused tomographic image data is displayed on the display device 29, it is possible to know the position of the affected area accurately. As in the case of Embodiment 2, this embodiment does not perform processing of separating X-ray image pickup signals and γ-ray image pickup signals from the output signal output from the radiation detector 4, but can create X-ray computed tomographic image data and obtain PET image data.

(Embodiment 7)

Figure 16:
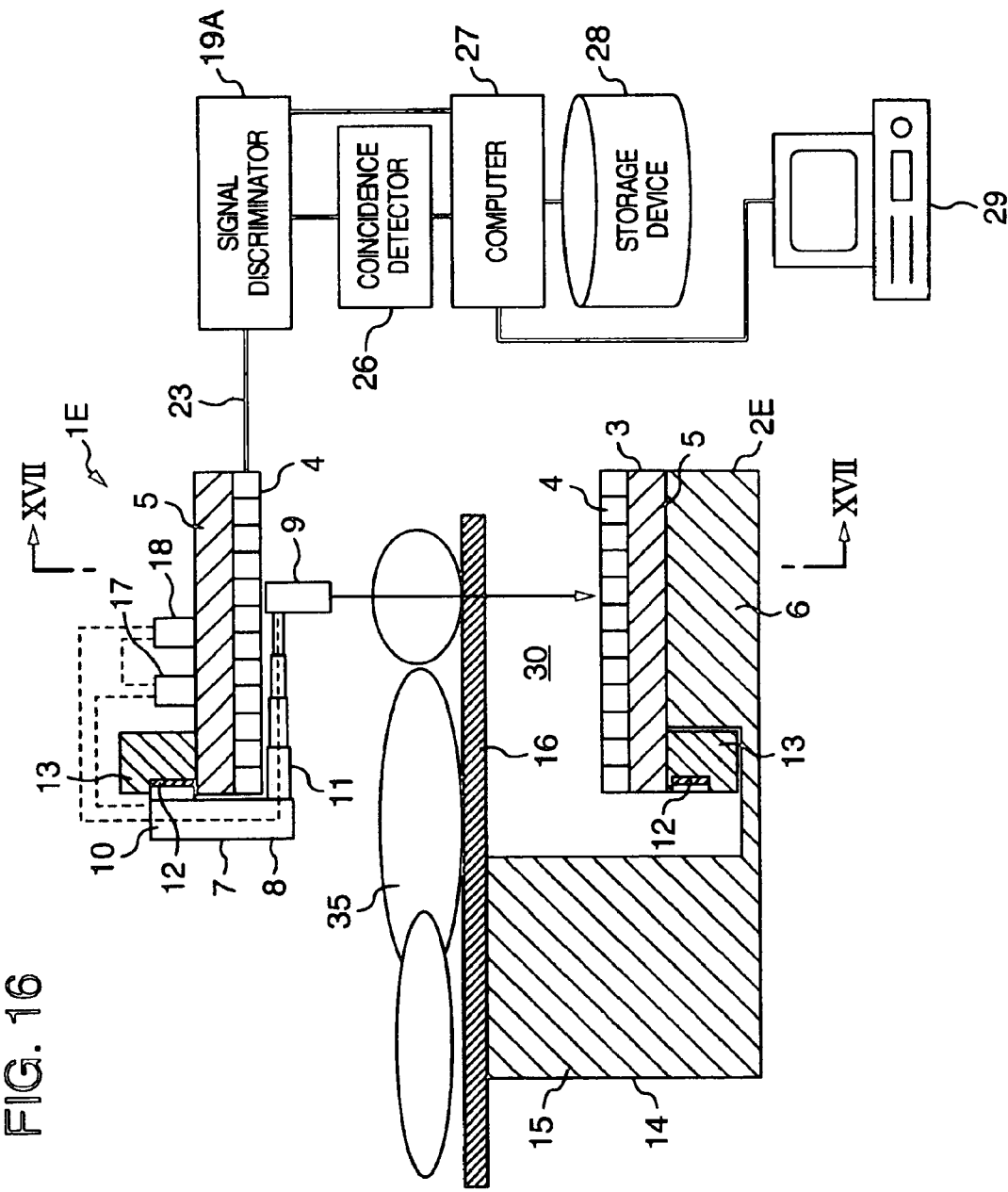
FIG. 16 is a longitudinal sectional view of a radiological imaging apparatus which is another embodiment of the present invention.
Figure 17:
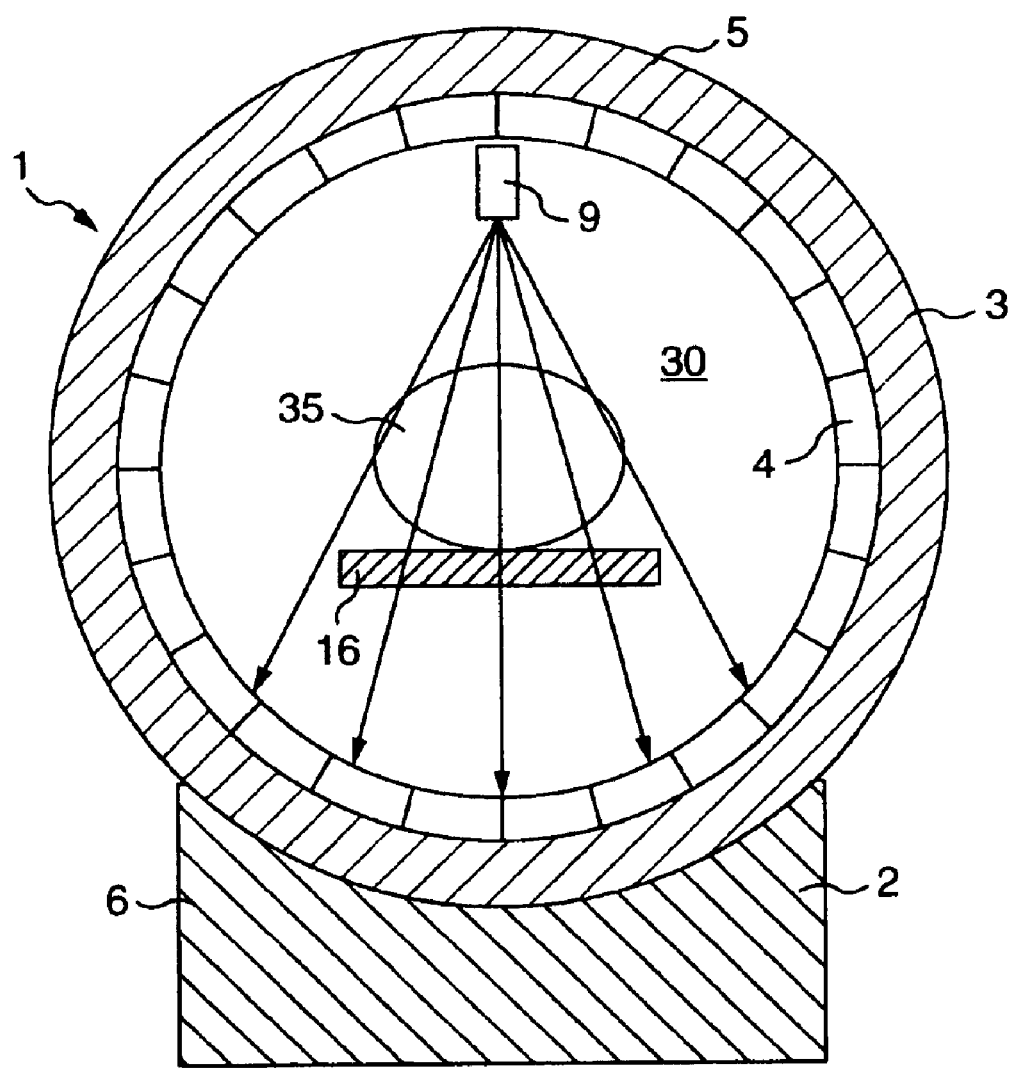
FIG. 17 is a sectional view at XVII—XVII of FIG. 16.

A radiological imaging apparatus according to another embodiment of the present invention will be explained based on FIG. 16 and FIG. 17. The radiological imaging apparatus 1 of this embodiment includes an image pickup apparatus 2D, an examinee holding apparatus 14, a signal discriminator 19A, a coincidence detector 26, a computer (e.g., workstation) 27, a storage device 28 and a display device 29. The examinee holding apparatus 14 includes a support 15, a bed 16 set on top of the support 15 in a manner movable in the longitudinal direction. The image pickup apparatus 2D is set in a direction perpendicular to the longitudinal direction of the bed 16 and includes a radiation detector ring structure 3, an X-ray source circumferential direction transfer unit 7, a drive controller 17, an X-ray source controller 18 and a casing (not shown). The radiation detector ring structure 3 includes a ring-shaped holding section 5 and multiple radiation detectors 4 set in a ring form inside the ring-shaped holding section 5. A through hole section 30 into which the bed 16 is inserted is formed inside the radiation detectors 4 of the radiation detector ring structure 3. Not only multiple radiation detectors 4 (approximately 10000 in total) are set in the circumferential direction of the ring-shaped holding section 5 but also a plurality of radiation detectors 4 is set in the axial direction of the through hole section 30. The radiation detector 4 is a semiconductor radiation detector and a semiconductor device of a cube of 5 mm per side which is the detection section is made of cadmium telluride (CdTe). The detection section may also be made of gallium arsenide (GaAs) or cadmium zinc telluride (CZT). The ring-shaped holding section 5 is set on top of the support 6. The supports 6 and 15 are mutually connected and fixed to the floor of the inspection room. The drive controller 17 and X-ray source controller 18 are set on the outer surface of the ring-shaped holding section 5. The radiation detector ring structure 3, drive controller 17 and X-ray source controller 18 are set in the casing.

The X-ray source circumferential direction transfer unit 7 includes the X-ray source apparatus 8 and a ring-shaped X-ray source holding section 13. The X-ray source holding section 13 is attached to the external surface of the ring-shaped holding section 5 at one end of the ring-shaped holding section 5. The ring-shaped guide rail 12 is set on one end face of the X-ray source holding section 13. The guide rail 12 and X-ray source holding section 13 surround the through hole section 30. The X-ray source apparatus 8 includes the X-ray source 9, X-ray source drive 10 and axial transfer arm 11. The X-ray source drive 10 includes a power transmission mechanism provided with a first motor (not shown) and a reduction gear mechanism in the casing. The power transmission mechanism is connected to the rotational axis of the first motor. The axial transfer arm 11 extends into the through hole section 30 attached to the casing of the X-ray source drive 10. The X-ray source 9 is attached to the axial transfer arm 11. The axial transfer arm 11 stretches in the axial direction of the through hole section 30 to move the X-ray source 9 in the axial direction of the through hole section 30. The axial transfer arm 11 is stretched by an action of a second motor (not shown) installed in the X-ray source drive 10. The X-ray source drive 10 is attached to the guide rails 12 so that it is movable along the guide rails 12 without dropping. The X-ray source drive 10 includes a pinion (not shown) to receive a rotational force from the above-described power transmission mechanism. This pinion engages with the rack provided on the guide rails 12.

The X-ray source 9 includes a publicly known X-ray tube (not shown). This X-ray tube has the same structure and function as those of the X-ray tube used in Embodiment 6 and generates 80 keV X-rays. These X-rays are radiated from the X-ray source 9.

Figure 8:
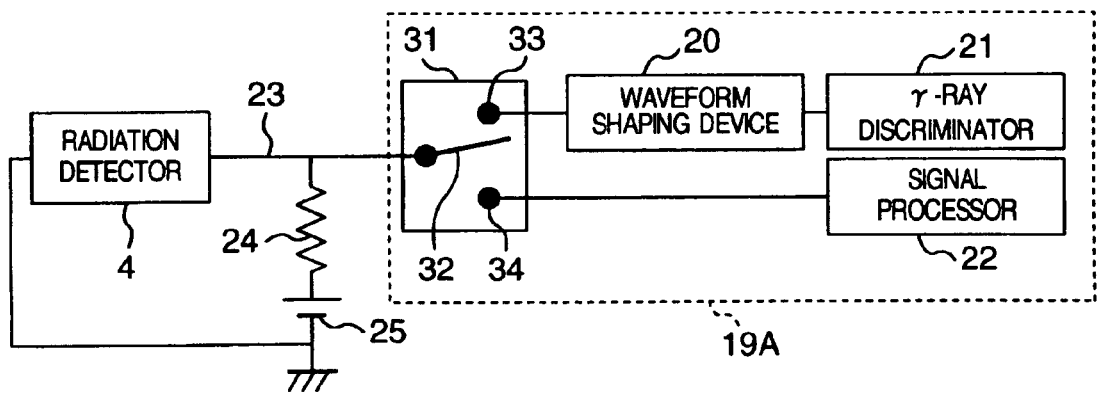
FIG. 8 illustrates another embodiment of the signal discriminator of the embodiment shown in FIG. 1.

The radiation detectors 4 are connected to their respective signal discriminators 19 via the wiring 23. One signal discriminator 19A whose configuration is shown in FIG. 8 is provided for each radiation detector 4. Each γ-ray discriminator 21 of the signal discriminator 19A is connected to the computer 27 via the coincidence detector 26. The number of the coincidence detectors 26 provided is one and connected to the γ-ray discriminator 21. The coincidence detector 26 can also be provided for every several γ-ray discriminators 21. Each signal processor 22 of the signal discriminator 19A is connected to the computer 27. The storage device 28 and display device 29 are connected to the computer 27. The signal discriminator 19A is a signal processor. This signal processor is provided with a first signal processor including the signal processor 22 and a second signal processor including a waveform shaping device 20 and γ-ray discriminator 21.

This embodiment is an example of conducting an X-ray computed tomographic inspection (act of detecting X-rays radiated from the X-ray source 9 and passing through the body of the examinee using a radiation detector) and a PET inspection (act of detecting γ-rays radiated from within the body of the examinee caused by PET radiopharmaceutical using a radiation detector) using a single image pickup apparatus 2D. This embodiment is also based on the principles of radiation detection explained in Embodiment 6. A specific X-ray irradiation time T calculated based on Expressions (1) and (2) can also be set to 1 μsec or less when radioactivity doses into the body are supposed to be 360 MBq or less.

Before conducting a radiation inspection, the examinee 35 is administered with PET radiopharmaceutical beforehand by means of injection so that radioactivity doses into the body are 370 MBq or less. The PET radiopharmaceutical are selected according to the inspection purpose (localizing cancer or inspecting the arterial flows of the heart, etc.). X-ray computed tomographic inspection and PET inspection are conducted by moving the bed 16 on which the examinee 35 administered with PET radiopharmaceutical is laid down and with the examinee 35 inserted in the through hole section 30 and using the image pickup apparatus 2.

The X-ray source controller 18 controls the time of emission of X-rays from the X-ray source 9 as in the case of Embodiment 6. When an X-ray computed tomographic inspection is started, the drive controller 17 outputs a drive start signal and closes a switch to a power supply connected to the first motor of the X-ray source drive 10 (hereinafter referred to as "first motor switch"). With a current supply, the first motor rotates and its rotational force is transmitted to the pinion via the power transmission mechanism and the pinion rotates. Since the pinion is engaged with the rack of the guide rails 12, the X-ray source apparatus 8, that is, the X-ray source 9 moves along the guide rails 12 in the circumferential direction. The X-ray source 9 moves around the examinee 35 inserted in the through hole section 30 at a set speed. When an X-ray computed tomographic inspection is finished, the drive controller 17 outputs a drive stop signal and opens the first motor switch. This stops the movement of the X-ray source 9 in the circumferential direction. In this embodiment, all radiation detectors 4 arranged in a ring form in the circumferential direction do not move in the circumferential direction nor move in the axial direction of the through hole section 30. A control signal is transmitted from the immobile X-ray source controller and drive controller to the mobile X-ray source using a publicly known technology that will not interfere with the movement of the X-ray source.

The drive start signal output from the drive controller 17 when starting an X-ray computed tomographic inspection is input to the X-ray source controller 18. The X-ray source controller 18 outputs an X-ray generation signal based on the input of the drive start signal. Then, X-ray source controller 18 outputs X-ray stop signals and X-ray generation signals repeatedly. By repeatedly outputting X-ray stop signals and X-ray generation signals, the X-ray source 9 radiates X-rays for a first set time, that is, 1 μsec and stops the emission of X-rays for a second set time. This emission and stop of emission of X-rays are repeated during a period of circumferential movement of the X-ray source 9. The X-rays radiated from the X-ray source 9 are irradiated in the form of fan beams onto the examinee 35 inserted in the through hole section 30. As the X-ray source 9 moves in the circumferential direction, the examinee 35 on the bed 16 is irradiated with X-rays from all directions. These X-rays pass through the examinee 35 and are detected by a plurality of radiation detectors 4 placed in the circumferential direction centered on the radiation detector 4 which is located at 180° from the X-ray source 9 with the axial center of the through hole section 30 as the base point. These radiation detectors 4 output X-ray image pickup signals. These X-ray image pickup signals are input to their respective signal discriminators 19A through their respective wirings 23. The radiation detectors 4 detecting the above-described X-rays are called "first radiation detectors 4" for the sake of convenience.

511 keV γ-rays caused by PET radiopharmaceutical are radiated from the examinee 35 on the bed 16 inserted into the through hole section 30. The radiation detectors 4 other than the first radiation detectors 4 detect γ-rays radiated from the examinee 35 and output γ-ray image pickup signals. These γ-ray image pickup signals are entered to their respective signal discriminators 19A through the respective wirings 23. The radiation detectors 4 that detect γ-rays are called "second radiation detectors 4" for the sake of convenience.

In the signal discriminators 19A, the γ-ray image pickup signals output from the second radiation detectors 4 are transmitted to the γ-ray discriminator 21 and the X-ray image pickup signals output from the first radiation detectors 4 are transmitted to the signal processor 22. These image pickup signals are transmitted through a changeover operation of the changeover switch 31 of the signal discriminator 19A. The changeover operation of connecting the movable terminal 32 of the changeover switch 31 to the fixed terminal 33 or fixed terminal 34 is performed based on a changeover control signal which is the output of the drive controller 17. The drive controller 17 controls the-transfer operation of the X-ray source drive 10 as described above, and at the same time selects the first radiation detectors 4 and connects the movable terminal 32 of the changeover switch 31 of the signal discriminator 19 connected to these first radiation detectors 4 to the fixed terminal 34.

The way how the first radiation detectors 4 are selected will be explained. An encoder (not shown) is connected to the first motor in the X-ray source drive 10. The drive controller 17 is fed a detection signal of the encoder and finds the position in the circumferential direction of the X-ray source drive 10, that is, the X-ray source 9 and selects the radiation detector 4 placed 180° opposite to the position of this X-ray source 9 using the stored data of the positions of the radiation detectors 4. The X-rays radiated from the X-ray source 9 has a certain breadth in the circumferential direction of the guide rails 12, and therefore there is a plurality of radiation detectors 4 that detect X-rays passing through the body of the examinee 35 in the circumferential direction in addition to the selected radiation detector 4. The drive controller 17 also selects the plurality of radiation detectors 4. These radiation detectors 4 are the first radiation detectors. As the X-ray source 9 moves in the circumferential direction, the first radiation detectors 4 also change. It seems that the first radiation detectors 4 also move in the circumferential direction together with the circumferential movement of the X-ray source 9. When the drive controller 17 selects another radiation detector 4 as the X-ray source 9 moves in the circumferential direction, the movable terminal 32 connected to the radiation detector 4 which becomes the new first radiation detector is connected to the fixed terminal 34. As the X-ray source 9 moves in the circumferential direction, the movable terminal 32 connected to a radiation detector 4 which is no more the first radiation detector 4 is connected to the fixed terminal 33 by the drive controller 17.

The first radiation detectors 4 can also be said as the radiation detectors 4 connected to the signal processor 22 by the changeover switch 31. The second radiation detectors 4 can also be said as the radiation detectors 4 connected to the γ-ray discriminator 21 by the changeover switch 31. The individual radiation detectors 4 installed in the ring-shaped holding section 5 sometimes become the first radiation detectors 4 or the second radiation detectors 4 depending on the relationship with the position of the X-ray source 9. Because of this, one radiation detector 4 outputs both an X-ray image pickup signal and γ-ray image pickup signal though separately.

The first radiation detectors 4 detect X-rays radiated from the X-ray source 9 for the first set time of 1 µsec and passing through the examinee 35. The probability that the first radiation detectors 4 detect γ-rays radiated from the examinee 35 for 1 µsec is as small as negligible as described above. Many γ-rays generated in the body of the examinee 35 caused by PET radiopharmaceutical are not radiated in a specific direction but in all directions. These γ-rays are paired and radiated in directions almost opposite to each other (180°±0.6°) as described above and are detected by any one of the second radiation detectors 4 of the radiation detector ring structure 3.

In the case where the position of the affected area of the examinee 35 is not specified beforehand, the bed 16 is moved to carry out PET inspections on the whole body of the examinee 35. While this PET inspection is being carried out, the X-ray source 9 is rotated in the circumferential direction and an X-ray computed tomographic inspection is carried out on the parts subject to a PET inspection. In the case where the position of the affected area of the examinee 35 is specified beforehand by other inspections, the bed 16 is moved so that the predetermined position of the affected area is inserted into the through hole section 30 and a PET inspection and X-ray computed tomographic inspection are carried out in the vicinity of the affected area using the image pickup apparatus 2.

Signal processing of the signal discriminator 19A when X-ray image pickup signals and γ-ray image pickup signals output from the radiation detectors 4 are input will be explained. The X-ray image pickup signals output from the first radiation detectors 4 are input to the signal processor 22 by an action of the changeover switch 31 as described above. The signal processor 22 integrates the X-ray image pickup signals input using an integrator and outputs the integrated value of the X-ray image pickup signals, that is, information on the intensity of the X-ray image pickup signals.

The γ-ray image pickup signals output from the second radiation detectors 4 are input to the waveform shaping device 20 by an action of the changeover switch 31. The waveform shaping device 20 converts γ-ray image pickup signals with the above-described waveform shown in FIG. 3 to γ-ray image pickup signals having a time Gaussian distribution waveform shown in FIG. 4 and outputs. The energy of γ-rays generated inside the body by annihilation of positrons emitted from PET radiopharmaceutical is 511 keV as described above. The γ-ray discriminator 21 generates pulse signals having predetermined energy as described in Embodiment 1 when an image pickup signal having energy equal to or greater than the first energy set value of 450 keV. The γ-ray discriminator 21 can be said to have a first filter as described in Embodiment 1.

The coincidence detector 26 is fed a pulse signal output from the γ-ray discriminator 21 of each signal discriminator 19A, carries out coincidence counting using these pulse signals and calculates a count rate for the γ-ray image pickup signal. Furthermore, the coincidence detector 26 stores data of two detection points at which a pair of γ-rays are detected with a pair of pulse signals corresponding to the pair of γ-ray (positions of a pair of radiation detectors 4 having a difference of almost 180° (strictly speaking 180°±0.6°) centered on the axial center of the through hole section 30) as position information of γ-ray detection.

Figure 18:
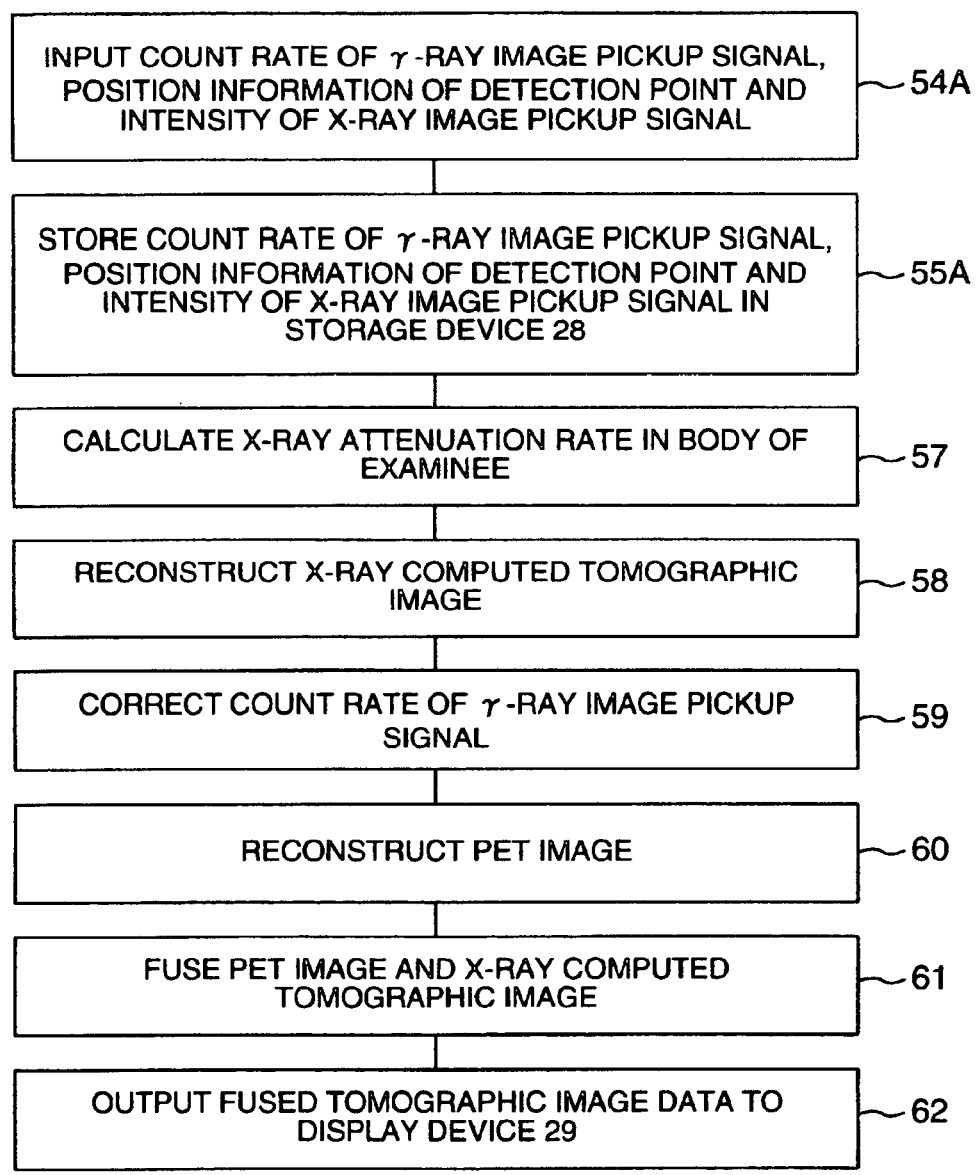
FIG. 18 is a flow chart of a procedure executed by the computer in FIG. 16.

The computer 27 executes processing according to the procedure in steps 54A, 55A, 57 to 62 shown in FIG. 18. The computer 27 that executes such processing is a tomographic data creation apparatus. The count rate of the γ-ray image pickup signal counted by the coincidence detector 26, position information of the detection points output from the coincidence detector 26 and the intensity of the X-ray image pickup signals output from the signal processor 22 are input (step 54A). The count rate of the γ-ray image pickup signal, position information of the detection points and the intensity of the X-ray image pickup signals which have been entered are stored in the storage device 28 (step 55A). The processing in steps 57 to 62 is carried out as in the case of Embodiment 1. In step 57, the attenuation rate of X-rays in each voxel is calculated using the intensity of X-ray image pickup signals extracted from the storage device 28. The fused tomographic image data is displayed on the display device 29.

By the way, an X-ray computed tomographic image requires a plurality of scan data pieces, and therefore it is possible to acquire the necessary amount of data from the radiation detectors 4 by moving the X-ray source 9 along the guide rails 12 using the X-ray source drive 10. Through this circumferential scanning of the X-ray source 9, this embodiment obtains two-dimensional sectional data about an X-ray image pickup signal on one cross section of the examinee 35. The two-dimensional sectional data about an X-ray image pickup signal on another cross section can be obtained by stretching the axial transfer arm 11 and moving the X-ray source 9 in the axial direction of the through hole section 30. By accumulating these two-dimensional sectional data pieces, it is possible to obtain three-dimensional sectional data. Using these three-dimensional sectional data, it is possible to obtain three-dimensional X-ray computed tomographic image data. Furthermore, by continuously stretching the axial transfer arm 11 in the axial direction of the through hole section 30 as the X-ray source 9 rotates, it is also possible to perform a helical scan of X-rays. Two-dimensional sectional data on the X-ray image pickup signal on another cross section can also be obtained by transferring the bed 16 in the axial direction of the through hole section 30 instead of stretching the axial transfer arm 11.

This embodiment can produce the following effects:

(1) In this embodiment, a plurality of radiation detectors 4 provided on the radiation detector ring structure 3 is arranged in a ring form. This embodiment allows these radiation detectors 4 arranged in a ring form to detect not only γ-rays radiated from the examinee 35 but also X-rays radiated from the X-ray source 9 moving in the circumferential direction and passing through the examinee 35. Thus, in contrast to the conventional technologies requiring an image pickup apparatus to detect penetrating X-rays and another image pickup apparatus to detect γ-rays as the image pickup apparatuses, this embodiment needs only one image pickup apparatus, which simplifies the configuration of the radiological imaging apparatus capable of executing both X-ray computed tomographic inspection and PET inspection.

(2) In this embodiment, each of the radiation detectors 4 arranged in a ring form outputs both an X-ray image pickup signal which is the detection signal of X-rays passing through the body of the examinee 35 (called "penetrating X-rays") and a γ-ray image pickup signal which is the detection signal of γ-rays radiated from within the body caused by radiopharmaceutical. This configuration also contributes to further simplification of the configuration of the radiological imaging apparatus and reduction of the size of the radiological imaging apparatus.

(3) This embodiment can reconstruct a first tomographic image (X-ray computed tomographic image) including images of internal organs and bones of the examinee 35 using an X-ray image pickup signal which is one of output signals of the radiation detectors 4 arranged in a ring form and reconstruct a second tomographic image (PET image) including an image of the affected area of the examinee 35 using a γ-ray image pickup signal which is another output signal of the radiation detector 4. Since the first tomographic image data and second tomographic image data are reconstructed based on output signals of the radiation detectors 4 that detect both the penetrating X-rays and γ-rays, it is possible to fuse the first tomographic image data and second tomographic image data positioned accurately. This makes it easier to obtain exact tomographic images (fused tomographic images) including the affected area, internal organs and bones. This fused tomographic image makes it possible to know the position of the affected area accurately in relation to internal organs and bones. For example, it is possible to easily obtain image data combining both tomographic images by aligning the first tomographic image data and second tomographic image data centered on the axial center of the through hole section 30 of the image pickup apparatus 2.

(4) This embodiment can obtain image pickup signals necessary to create a first tomographic image and image pickup signals necessary to create a second tomographic image from the shared radiation detectors 4, and can thereby shorten the time required to inspect the examinee 35 (inspection time) significantly. In other words, this embodiment can obtain image pickup signals necessary to create a first tomographic image and image pickup signals necessary to create a second tomographic image in a short inspection time. This embodiment eliminates the need to move the examinee from one image pickup apparatus to detect penetrating X-rays to another image pickup apparatus to detect γ-rays in the case of the conventional art, and can thereby reduce the probability that the examinee will move. Eliminating the need to move the examinee from one image pickup apparatus to detect penetrating X-rays to another image pickup apparatus to detect γ-rays also contributes to shortening the time for inspecting the examinee.

(5) This embodiment rotates the X-ray source 9 and does not move the radiation detector ring structure 3, that is, the radiation detectors 4 in the circumferential direction and axial direction of the through hole section 30, and can thereby reduce the capacity of the motor to rotate the X-ray source 9 compared to the motor necessary to move the radiation detector ring structure 3. It is also possible to reduce power consumption required to drive the motor of the latter compared to that of the motor of the former.

(6) Since the number of γ-ray image pickup signals input to the signal processor 22, that is, the first signal processor is reduced significantly, it is possible to obtain exact first tomographic image data. Thus, using image data obtained by combining the first tomographic image data and second tomographic image data makes it possible to know the position of the affected area precisely.

(7) In this embodiment, the X-ray source 9 rotates inside the radiation detectors 4 arranged in a ring form, and therefore the diameter of the ring-shaped holding section 5 increases and the number of radiation detectors 4 that can be placed in the circumferential direction inside the ring-shaped holding section 5 can be increased. This increase in the number of radiation detectors 4 in the circumferential direction results in an improvement of sensitivity and an improvement of resolution on the cross section of the examinee 35.

(8) In this embodiment, because of the locations of the axial transfer arm 11 to which the X-ray source 9 is attached and the X-ray source 9 inside the radiation detectors 4, there is a possibility that they will block γ-rays radiated from the examinee 35 preventing the radiation detectors 4 located right behind them from detecting γ-rays and losing detection data necessary to create a PET image. However, since the X-ray source 9 and axial transfer arm 11 are rotated in the circumferential direction by the X-ray source drive 10 in this embodiment as described above, loss of data is practically not a problem. Especially, the rotational speed of the X-ray source 9 and axial transfer arm 11 is approximately 1 sec/slice, and therefore it is sufficiently short when compared to a time required for a PET inspection which is on the order of a few minutes at a minimum. Loss of data is therefore practically no problem from this aspect, too. Furthermore, when X-ray computed tomographic inspection is not performed, equipment related to X-ray computed tomographic inspection can be removed from the radiation detectors 4 and housed. For example, this embodiment adopts a configuration with the X-ray source 9 housed in the X-ray source drive 10.

(Embodiment 8)

Figure 19:
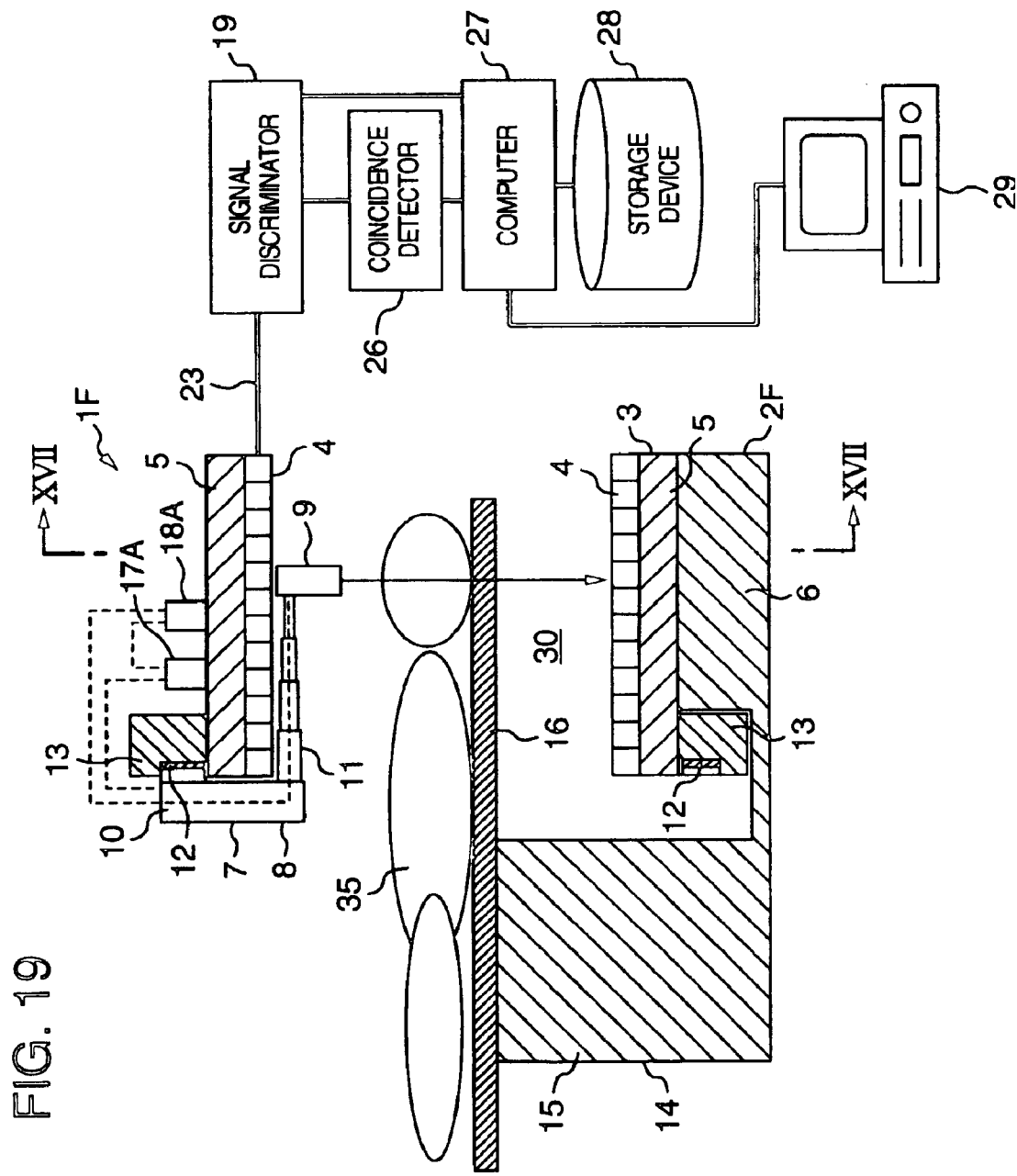
FIG. 19 is a longitudinal sectional view of a radiological imaging apparatus which is another embodiment of the present invention.

A radiological imaging apparatus 1F according to Embodiment 7 which is another embodiment of the present invention will be explained using FIG. 19 below. The radiological imaging apparatus 1F replaces the image pickup apparatus 2E of the radiological imaging apparatus 1E in Embodiment 7 with an image pickup apparatus 2F and replaces the signal discriminator 19A with the signal discriminator 19 shown in FIG. 2. The remaining configuration of the radiological imaging apparatus 1F is the same as the configuration of the radiological imaging apparatus 1E. Since the radiological imaging apparatus 1F is provided with the signal discriminator 19, the computer 27 executes processing shown in FIG. 5. The image pickup apparatus 2F has a configuration with the drive controller 17 and X-ray source controller 18 of the image pickup apparatus 2E in Embodiment 7 replaced with a drive controller 17A and X-ray source controller 18A, respectively. The remaining configuration of the image pickup apparatus 2F is the same as that of the image pickup apparatus 2E. One signal discriminator 19 is provided for each radiation detector 4. A pulse height analyzer 38 of the signal discriminator 19 is connected to the computer 27. The γ-ray discriminator 21 of the signal discriminator 19 is connected to the computer 27 via a coincidence detector 26. The signal discriminator 19A is a signal processor and provided with a first signal processor having the pulse height analyzer 38 and a second signal processor having a waveform shaping device 20 and γ-ray discriminator 21. The drive controller 17A and X-ray source controller 18A are mounted on a ring-shaped holding section 5.

This embodiment shows an example of performing an X-ray computed tomographic inspection and PET inspection using one image pickup apparatus 2F. 511 keV γ-rays radiated from the affected area of the examinee 35 who is administered with PET radiopharmaceutical and laid down on the bed 16 while being inserted into the through hole section 30 are detected by the radiation detectors 4. On the other hand, X-rays (80 keV) irradiated from the X-ray source 9 are detected by the radiation detectors 4 after passing through the examinee 35. The rotational operation of the X-ray source 9 during an X-ray computed tomographic inspection is the same as that of Embodiment 7. X-rays and γ-rays are detected in the same way as in Embodiment 1. The radiation detectors 4 at locations where X-rays radiated from the X-ray source 9 do not reach (e.g., radiation detectors 4 away from the X-ray source 9 in the axial direction of the through hole section 30) detect γ-rays unless the X-ray source 9 moves in the axial direction. The drive controller 17A of this embodiment outputs a drive start signal and drive stop signal to control movements of the X-ray source drive 10 in the same way as for the drive controller 17 in Embodiment 1. However, the drive controller 17A does not perform changeover control over the changeover switch 31 carried out by the drive controller 17. The X-ray source controller 18A outputs an X-ray generation signal to close the X-ray source switch as in the case of Embodiment 1 and outputs an X-ray stop signal to open the X-ray source switch. However, the X-ray source controller 18A does not perform control in such a way as to generate X-rays only for a first set time during which γ-rays incident upon the radiation detectors 4 are negligible as in the case of the X-ray source controller 18 in Embodiment 1. Thus, in this embodiment, even the radiation detectors 4 which are detecting X-rays also detect γ-rays. Therefore, in this embodiment which performs X-ray computed tomographic inspection and PET inspection using one image pickup apparatus 2A, each radiation detector 4 outputs an output signal including X-ray image pickup signal and γ-ray image pickup signal. The output signals from the radiation detectors 4 are input to their respective signal discriminators 19.

The signal discriminator 19 executes processing of X-ray image pickup signals and γ-ray image pickup signals as in the case of Embodiment 1. This embodiment uses the signal discriminators 19 to separate γ-ray image pickup signals and X-ray image pickup signals having different energy levels with respect to a peak count rate from the image pickup signals output from the radiation detectors 4. The coincidence detector 26 simulateously calculates a count rate with respect to a γ-ray image pickup signal using a pulse signal output from each γ-ray discriminator 21 of each signal discriminator 19 and outputs this count rate to the computer 27. The pulse height analyzer 38 outputs the count rates of the X-ray image pickup signals to the computer 27. The computer 27 executes processing based on the procedure in steps 54 to 62 shown in FIG. 5. Fused tomographic image data obtained by combining the first tomographic image data and second tomographic image data is displayed on the display device 29.

This embodiment can produce the effects (1) to (5), (7) and (8) in Embodiment 1. Furthermore, this embodiment can also produce the effects (9) and (10) below.

(9) This embodiment can separate X-ray image pickup signals and γ-ray image pickup signals from output signals from the radiation detectors 4. Thus, this embodiment can easily create first tomographic image data using the separated X-ray image pickup signals and second tomographic image data using the separated γ-ray image pickup signals. Furthermore, this embodiment can easily fuse the first tomographic image data and second tomographic image data as in the case of Embodiment 1.

(10) The semiconductor radiation detectors used as the radiation detectors 4 have high energy resolution. Thus, this embodiment can easily separate X-ray image pickup signals and γ-ray image pickup signals output from the radiation detectors 4 using the signal discriminator 19A.

(Embodiment 9)

Figure 20:
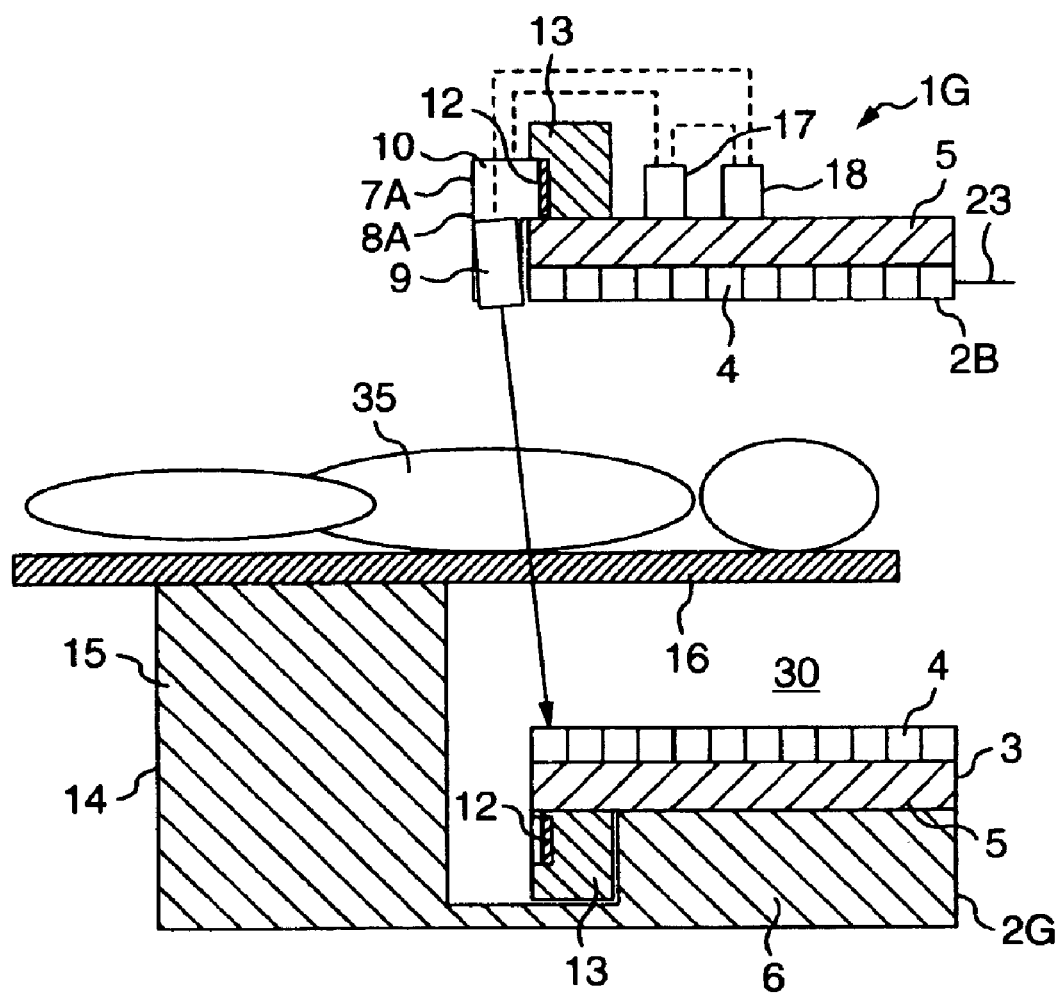
FIG. 20 is a longitudinal sectional view of a radiological imaging apparatus which is another embodiment of the present invention.

A radiological imaging apparatus 1G which is another embodiment of the present invention will be explained using FIG. 20 below. The radiological imaging apparatus 1G has a configuration of an image pickup apparatus 2G slightly changed from the configuration of the image pickup apparatus 2E in Embodiment 7. That is, the image pickup apparatus 2G has the configuration of the image pickup apparatus 2E with the X-ray source circumferential direction transfer device 7 replaced with an X-ray source circumferential direction transfer device 7A. The remaining configuration of the radiological imaging apparatus 1G is the same as that of the radiological imaging apparatus 1E. The X-ray source circumferential direction transfer device 7A includes an X-ray source apparatus 8A and a ring-shaped X-ray source holding section 13. The X-ray source holding section 13 of this embodiment has the same configuration as that of Embodiment 7. The X-ray source apparatus 8A includes an X-ray source 9 and an X-ray source drive 10 and does not have any axial transfer arm 8. In this embodiment, the X-ray source 9 is placed in such a way as to face one end face of the radiation detector ring structure 3, that is, placed next to one end face thereof. The X-ray source 9 placed as shown above is attached to the casing of the X-ray source drive 10 inclined in the axial direction of the through hole section 30 so that the X-ray emission orifice may face the radiation detector 4 placed 180° opposite to the X-ray source 9 at the radiation detector 4 of the radiation detector ring structure 3. The casing of the X-ray source drive 10 in this embodiment is shorter than the casing of the X-ray source drive 10 in Embodiment 7.

As in the case of Embodiment 7, this embodiment also performs a PET inspection and X-ray computed tomographic inspection using a single image pickup apparatus. A PET inspection in this embodiment is performed by detecting γ-rays radiated from the examinee 35 caused by PET radiopharmaceutical using the second radiation detectors 4 in the same way as for Embodiment 7. An X-ray computed tomographic inspection is performed by rotating the X-ray source apparatus 8A along the guide rails 12 as in the case of Embodiment 1 where the X-ray source apparatus 8 is rotated. During a PET inspection or X-ray computed tomographic inspection, the examinee 35 on the bed 16 is moved in the axial direction. In this embodiment, X-rays are irradiated diagonally from the inclined X-ray source 9 onto the examinee 35 and pass through the body of the examinee 35 diagonally. These penetrating X-rays are detected by the first radiation detectors 4. In this embodiment, the first radiation detectors 4 are located at an end of the radiation detector ring structure 3 facing the X-ray source apparatus 8. Processing of obtaining fused tomographic image data of the X-ray image pickup signals output from the first radiation detectors 4 and γ-ray image pickup signals output from the second radiation detectors 4 is performed in the same way as for Embodiment 7. This embodiment obtains X-ray computed tomographic images using X-ray image pickup signals for X-rays passing through the body of the examinee 35 diagonally and therefore it is necessary to incline the X-ray source 9 at an angle that will not deteriorate the accuracy of the X-ray computed tomographic images.

This embodiment can produce the effects (1) to (6) in Embodiment 7. This embodiment can further produce the following effects (11) to (13).

(11) Since the X-ray source 9 in this embodiment rotates next to the radiation detector ring structure 3 in which the radiation detectors 4 are set in a ring form, the diameter of the ring-shaped holding section 5 is reduced. This reduces the distance between two radiation detectors 4 placed 180° opposite to each other, making it possible to improve the quality of a PET image. A pair of γ-rays generated in the body of the examinee 35 are radiated in a direction of not completely 180°, but 180°±0.6°. When the distance between these radiation detectors 4 increases, the influence of ±0.6° increases, producing a slight difference between the two detection points corresponding to the pair of γ-rays specified by the coincidence detector 26. When the distance between those radiation detectors 4 is small, the influence of ±0.6° also decreases, making the two detection points corresponding to the pair of γ-rays specified by the coincidence detector 26 come closer to the true positions. This improves the quality of a PET image in this embodiment.

(12) Since the X-ray source 9 in this embodiment rotates next to the radiation detector ring structure 3 in which the radiation detectors 4 are set in a ring form, there are no objects blocking γ-ray radiated from the examinee 35 in front of the radiation detectors 4 as in the case of the X-ray source 9 and axial transfer arm 11 in Embodiment 7. Thus, this embodiment has no problems of loss of detected data as in the case of Embodiment 7.

(13) Since the diameter of the radiation detector ring structure 3 is reduced, this embodiment makes it possible to further reduce the size of the radiological imaging apparatus compared to Embodiment 1.

By continuously moving the examinee 35 inside the through hole section 30 using the bed 16 of the examinee holding apparatus 14 as the X-ray source 9 rotates in the circumferential direction, this embodiment can also perform an X-ray helical scan.

(Embodiment 10)

Figure 21:
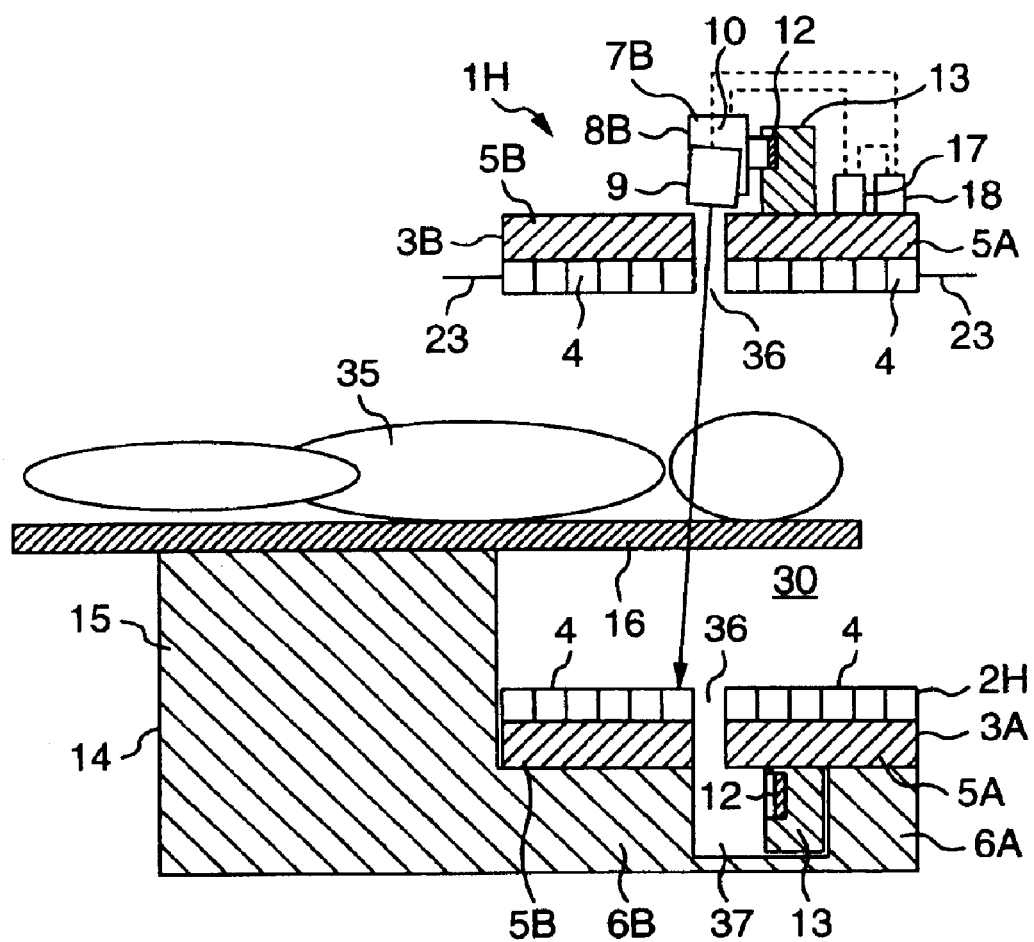
FIG. 21 is a longitudinal sectional view of a radiological imaging apparatus which is another embodiment of the present invention.

A radiological imaging apparatus of Embodiment 10 which is another embodiment of the present invention will be explained based on FIG. 21 below. The radiological imaging apparatus 1H of this embodiment has a configuration with the image pickup apparatus 2E in the radiological imaging apparatus 1E replaced with an image pickup apparatus 2H. The remaining configuration of the radiological imaging apparatus 1H is the same as that of the radiological imaging apparatus 1E. The image pickup apparatus 2H includes a pair of radiation detector ring structures 3A and 3B. The radiation detector ring structure 3A includes a ring-shaped holding section 5A and multiple radiation detectors 4 installed in a ring form inside the ring-shaped holding section 5A as in the case of Embodiment 7. The radiation detector ring structure 3B includes a ring-shaped holding section 5B and multiple radiation detectors 4 installed in a ring form inside the ring-shaped holding section 5B as in the case of Embodiment 7. The radiation detectors 4 provided for the radiation detector ring structures 3A and 3B are the same as the radiation detectors 4 used in Embodiment 7. The radiation detectors 4 provided for the radiation detector ring structures 3A and 3B are connected to their respective signal discriminators 19A, or more specifically, to their respective changeover switches 31 of the signal discriminators 19A through wirings 23 as in the case of Embodiment 7. A through hole section 30 into which a bed 16 is inserted is formed inside the radiation detectors 4 on the radiation detector ring structures 3A and 3B. The radiation detector ring structure 3A and radiation detector ring structure 3B are placed adjacent to each other so as to form a slit (gap) 36 in between. The slit 36 is formed all the circumference of the radiation detector ring structure. The radiation detector ring structure 3A is attached to a support 6A which fixes the ring-shaped holding section 5A to the floor. The radiation detector ring structure 3B is attached to a support 6B which fixes the ring-shaped holding section 5B to the floor. The axial center of the radiation detector ring structure 3A aligns with the axial center of the radiation detector ring structure 3B and the ring-shaped holding sections 5A and 5B have the same inner diameter and outer diameter.

Furthermore, the image pickup apparatus 2H is also provided with an X-ray source circumferential direction transfer apparatus 7B having an X-ray source apparatus 8B and a ring-shaped X-ray source apparatus holding section 13. The X-ray source apparatus holding section 13 of the X-ray source circumferential direction transfer apparatus 7B has the same configuration as that of Embodiment 7 and is attached to the outer surface of the ring-shaped holding section 5A. The X-ray source apparatus 8B includes an X-ray source 9 and X-ray source drive 10 and has no axial transfer arm 11. In this embodiment, the X-ray source 9 is located outside the ring-shaped holding sections 5A and 5B and faces the slit 36. The X-ray source 9 is attached to the casing of the X-ray source drive 10 inclined with respect to the axial direction of the through hole section 30 in such a way that the X-ray emission orifice may face the radiation detector 4 placed 180° opposite to the X-ray source 9 at the radiation detector 4 of the radiation detector ring structure 3B.

As in the case of Embodiment 7, this embodiment also carries out a PET inspection and X-ray computed tomographic inspection using a single image pickup apparatus. A PET inspection in this embodiment is performed by detecting γ-rays radiated from the examinee 35 caused by PET radiopharmaceutical using the second radiation detectors 4 in the same way as for Embodiment 7. An X-ray computed tomographic inspection is performed by rotating the X-ray source apparatus 8B along the guide rails 12 around the examinee 35 as in the case of Embodiment 7 where the X-ray source apparatus 8 is rotated. During a PET inspection or X-ray computed tomographic inspection, the examinee 35 is moved in the axial direction as in the case of Embodiment 9. In this embodiment, to allow the X-ray source apparatus 8B to rotate smoothly, a space 37 is formed between the support 6B and X-ray source apparatus holding section 13 outside the ring-shaped holding section 5A. The X-ray source apparatus 8B passes through this space 37 when it rotates. In this embodiment, X-rays radiated from the inclined X-ray source 9 and passing through the slit 36 are diagonally irradiated onto the examinee 35 laid down on the bed 16 and pass through the body of the examinee 35 diagonally. These passing X-rays are detected by the first radiation detectors 4. In this embodiment, the first radiation detectors 4 are located at one end of the radiation detector ring structure 3B facing the X-ray source 9. Since the X-rays radiated from the X-ray source 9 have a certain breadth, the first radiation detectors 4 also exist on one end face of the radiation detector ring structure 3A facing the radiation detector ring structure 3B. The first radiation detectors 4 move in the circumferential direction of the radiation detector ring structure as the X-ray source 9 rotates as in the case of Embodiment 1.

Processing of obtaining fused tomographic image data using the X-ray image pickup signal output from the first radiation detectors 4 and γ-ray image pickup signal output from the second radiation detectors 4 is performed in the same way as for Embodiment 7. This embodiment obtains X-ray computed tomographic images using X-ray image pickup signals for X-rays passing through the body of the examinee 35 diagonally, and therefore it is necessary to incline the X-ray source 9 at an angle that will not deteriorate the accuracy of the X-ray computed tomographic images.

This embodiment can produce the effects (1) to (6) in Embodiment 7 and can further produce the following effects (11) to (13) in Embodiment 9.

In this embodiment, it is also possible to stretch the X-ray source drive 10 toward the radiation detector ring structure 3B and attach to the casing of the X-ray source drive 10 inclined with respect to the axial direction of the through hole section 30 so that the X-ray emission orifice in the X-ray source 9 may face the radiation detector 4 placed 180° opposite to the X-ray source 9 at the radiation detector 4 of the radiation detector ring structure 3A. It is also possible to attach the X-ray source apparatus holding section 13 to the ring-shaped holding section 5B and incline it so that the X-ray emission orifice of the X-ray source 9 faces the radiation detectors 4 of the radiation detector ring structure 3A.

(Embodiment 11)

Figure 22:
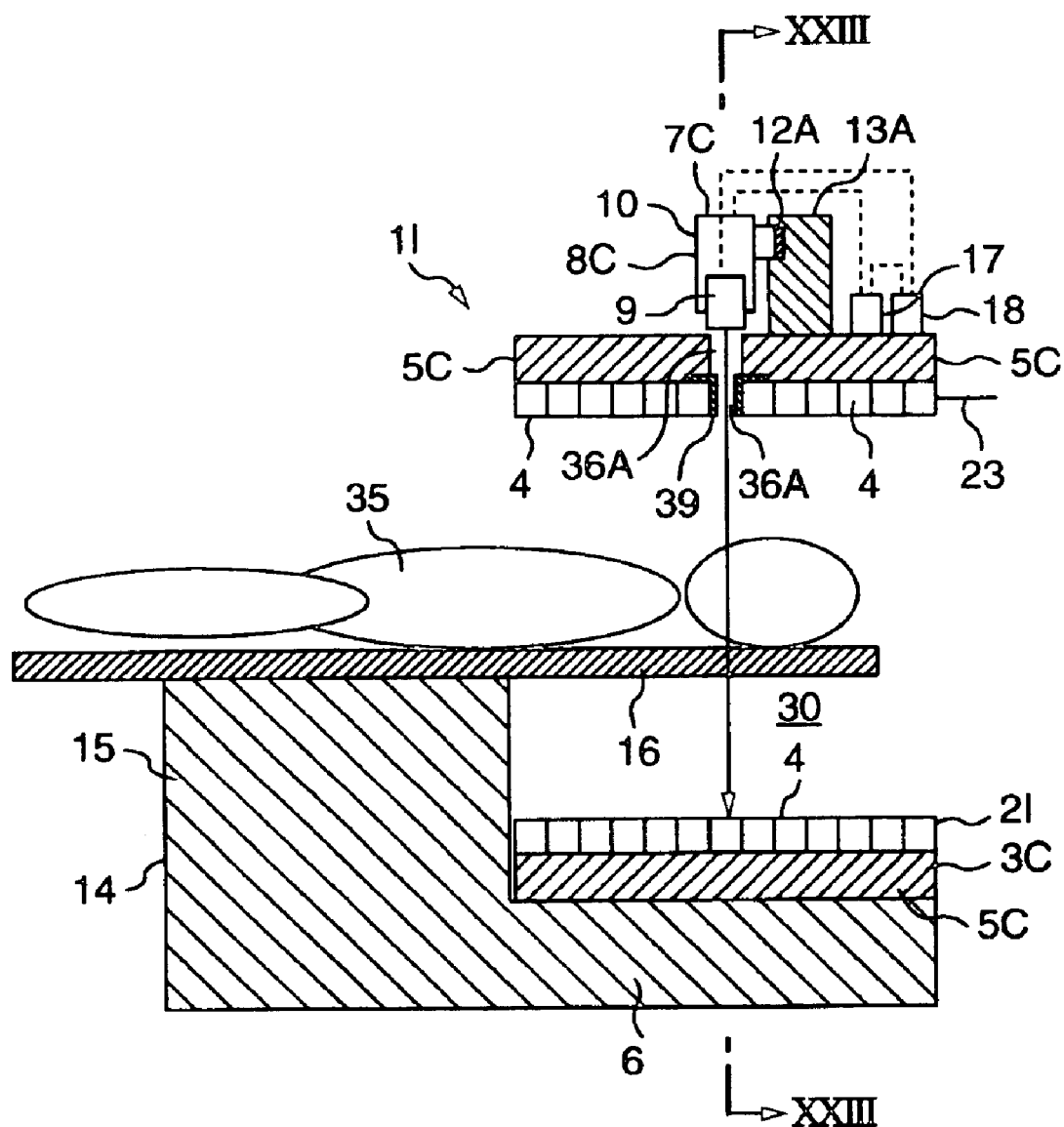
FIG. 22 is a longitudinal sectional view of a radiological imaging apparatus which is another embodiment of the present invention.
Figure 23:
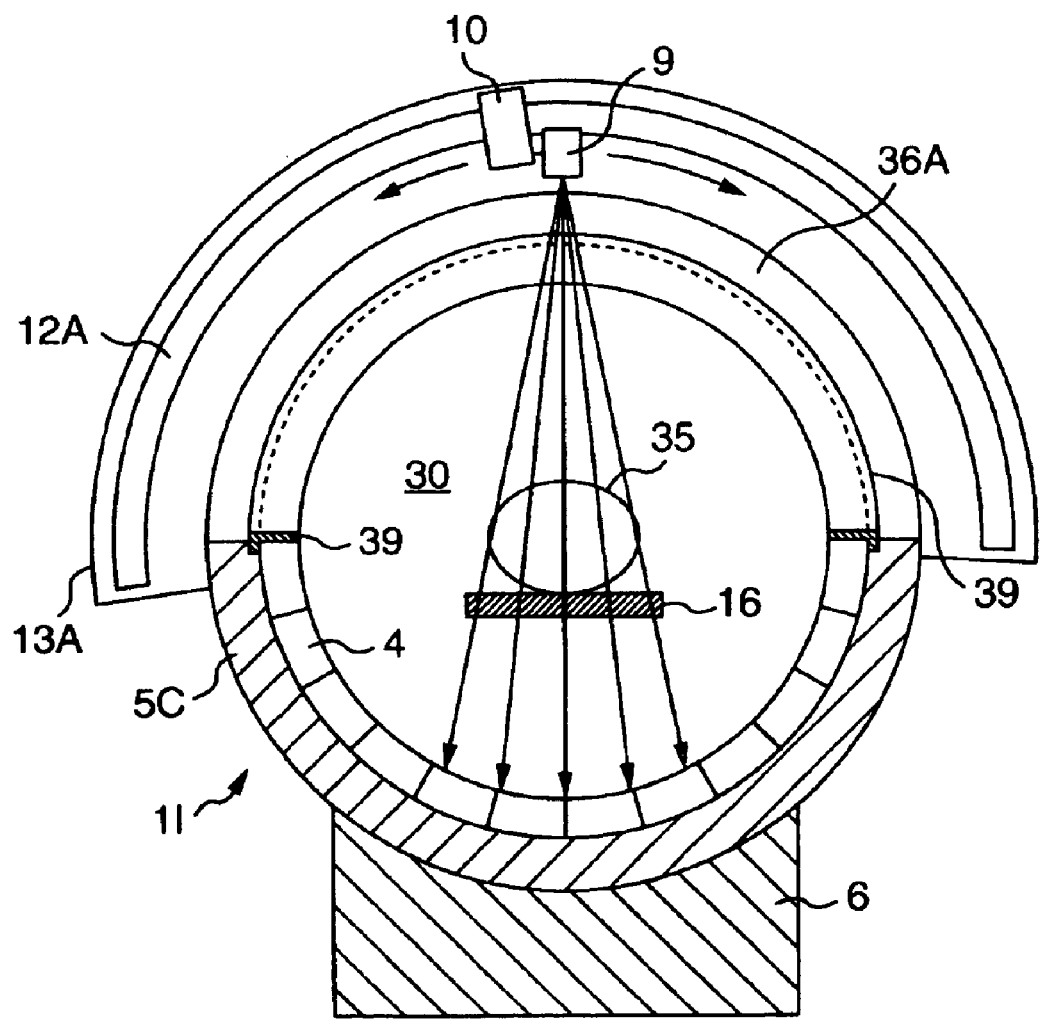
FIG. 23 is a sectional view at XXIII—XXIII of FIG. 22.

A radiological imaging apparatus 1I of Embodiment 11 which is another embodiment of the present invention will be explained based on FIG. 22 and FIG. 23 below. The radiological imaging apparatus 1I of this embodiment includes an image pickup apparatus 2I and has the same configuration as that of the radiological imaging apparatus 1E except the image pickup apparatus 2I. The image pickup apparatus 2I includes a radiation detector ring structure 3C and an X-ray source circumferential direction transfer device 7C. The radiation detector ring structure 3C includes multiple radiation detectors 4 on the inner surface of the ring-shaped holding section 5C installed in the support 6 as in the case of Embodiment 1. The ring-shaped holding section 5C has a slit 36A which is a through hole incised over a range of 180°. The slit 36A is located in the upper half of the ring-shaped holding section 5C. No radiation detectors 4 are placed in the section of the slit 36A. A collimator 39 is set in the slit 36A inside the ring-shaped holding section 5C. The collimator 39 is made of lead. The radiation detectors 4 are placed outside the collimator 39.

The X-ray source circumferential direction transfer device 7C is placed outside the ring-shaped support as in the case of the X-ray source circumferential direction transfer device 7B in Embodiment 10 and a quasi-semicircular X-ray source apparatus holding section 13A is placed on the outer surface of the upper part of the ring-shaped holding section 5C. A semicircular guide rail 12A is attached to the X-ray source apparatus holding section 13A. The X-ray source circumferential direction transfer device 7C is provided with an X-ray source apparatus 8C having an X-ray source 9 and X-ray source drive 10. The X-ray source apparatus 8C is different from the X-ray source apparatus 8B only in that the X-ray source 9 is attached to the X-ray source drive 10 so that the X-ray emission orifice of the X-ray source 9 is oriented in the direction perpendicular to the axial center of the through hole section 30.

This embodiment also performs a PET inspection and X-ray computed tomographic inspection on the examinee 35 who is laid down on the bed 16 administered with PET radiopharmaceutical using a single image pickup apparatus 2I. During a PET inspection or X-ray computed tomographic inspection, the examinee 35 is moved in the axial direction as in the case of Embodiment 9. An X-ray computed tomographic inspection is performed by irradiating the examinee 35 with the X-rays radiated from the X-ray source 9 and passing through the slit 36A and collimator 39. Irradiating the examinee 35 with the X-rays passing through the slit is the same as Embodiment 4. A PET inspection in this embodiment is performed by detecting γ-rays radiated from the examinee 35 using the second radiation detectors 4 as in the case of Embodiment 7 and an X-ray computed tomographic inspection is performed by detecting the X-rays passing through the examinee 35 using the first radiation detector 4.

In this embodiment, an X-ray computed tomographic inspection is performed by moving the X-ray source drive 10 of the X-ray source 9 along the guide rails 12A around the examinee 35 within a range of 180° to obtain an X-ray image pickup signal using the first radiation detectors 4. Two-dimensional sectional data of the X-ray computed tomographic image is obtained through processing of the computer 27 using this X-ray image pickup signal. Other two-dimensional sectional data can be created using X-ray image pickup signals obtained by moving the examinee 35 in the axial direction of the through hole section 30 and along the guide rail 12A of the X-ray source 9. By stacking these two-dimensional sectional data one atop another, it is possible to obtain three-dimensional sectional data of an X-ray computed tomographic image. Furthermore, by continuously moving the examinee 35 as the X-ray source 9 rotates in the circumferential direction, it is also possible to perform a pseudo-helical scan of X-rays. However, in this embodiment where the X-ray source 9 can only move within a 180° range, it is also possible to perform a pseudo-helical scan by continuously repeating to-and-fro motion of the X-ray source 9.

This embodiment can produce the effects (1) to (6) in Embodiment 7 and can also produce the effects (11) to (13) in Embodiment 9. This embodiment can further produce the following effects (14) and (15).

(14) The radiation shielding function of the collimator 39 prevents X-rays from entering the radiation detectors 4 adjacent to the slit 36A. Furthermore, the collimator 39 collimates the X-rays radiated from the X-ray source 9 in the form of fan beams.

(15) The X-ray source 9 weighs less than when the collimator is mounted on the following X-ray source 9, and therefore when the X-ray source 9 is moved by the X-ray source drive 10, the load applied to the X-ray source drive 10 decreases. This reduces power consumption by the first motor of the X-ray source drive 10.

Instead of the collimator 39 provided for the ring-shaped holding section 5C, the collimator may also be attached to the X-ray source 9. This collimator suppresses the spread of X-rays in the axial direction of the through hole section 30, and therefore it is possible to reduce the breadth of the slit 36A. Therefore, no X-rays enter the radiation detectors 4 adjacent to the slit 36A.

On the ring-shaped holding section 5C, it is also possible to form a plurality of slits 36A close to one another in the axial direction of the ring-shaped holding section 5C. In this case, the X-ray source 9 is placed outward away from the ring-shaped holding section 5C so that X-rays radiated from the X-ray source 9 can pass through the slits 36A. The X-rays passing through the plurality of slits 36A can be detected by their respective first radiation detectors 4 located in different positions in the axial direction of the ring-shaped holding section 5C. This configuration makes it possible to obtain X-ray image pickup signals capable of creating a plurality of two-dimensional sectional data of X-ray computed tomographic images coincidently by scanning the X-ray source 9 in the circumferential direction one time. This allows highly efficient X-ray computed tomographic inspection.

(Embodiment 12)

Figure 24:
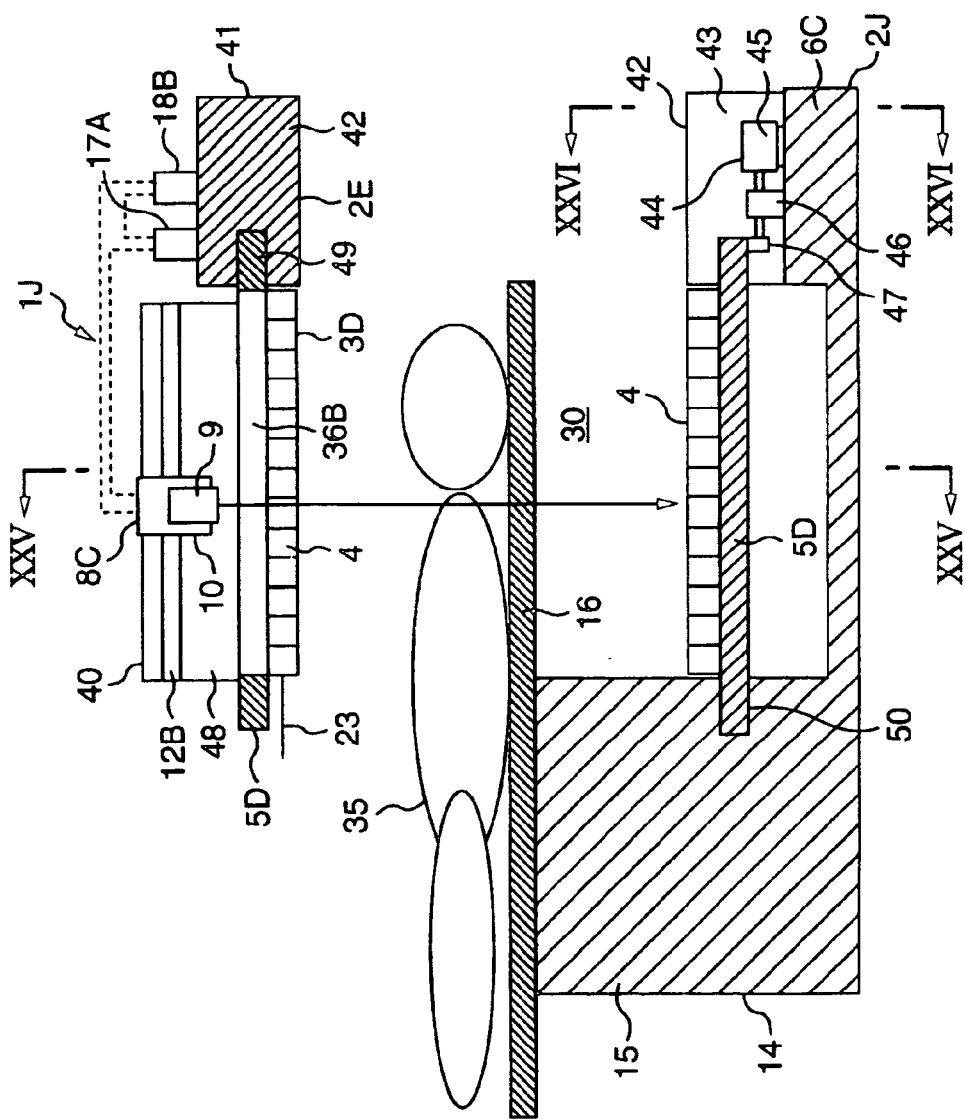
FIG. 24 is a longitudinal sectional view of a radiological imaging apparatus which is another embodiment of the present invention.
Figure 25:
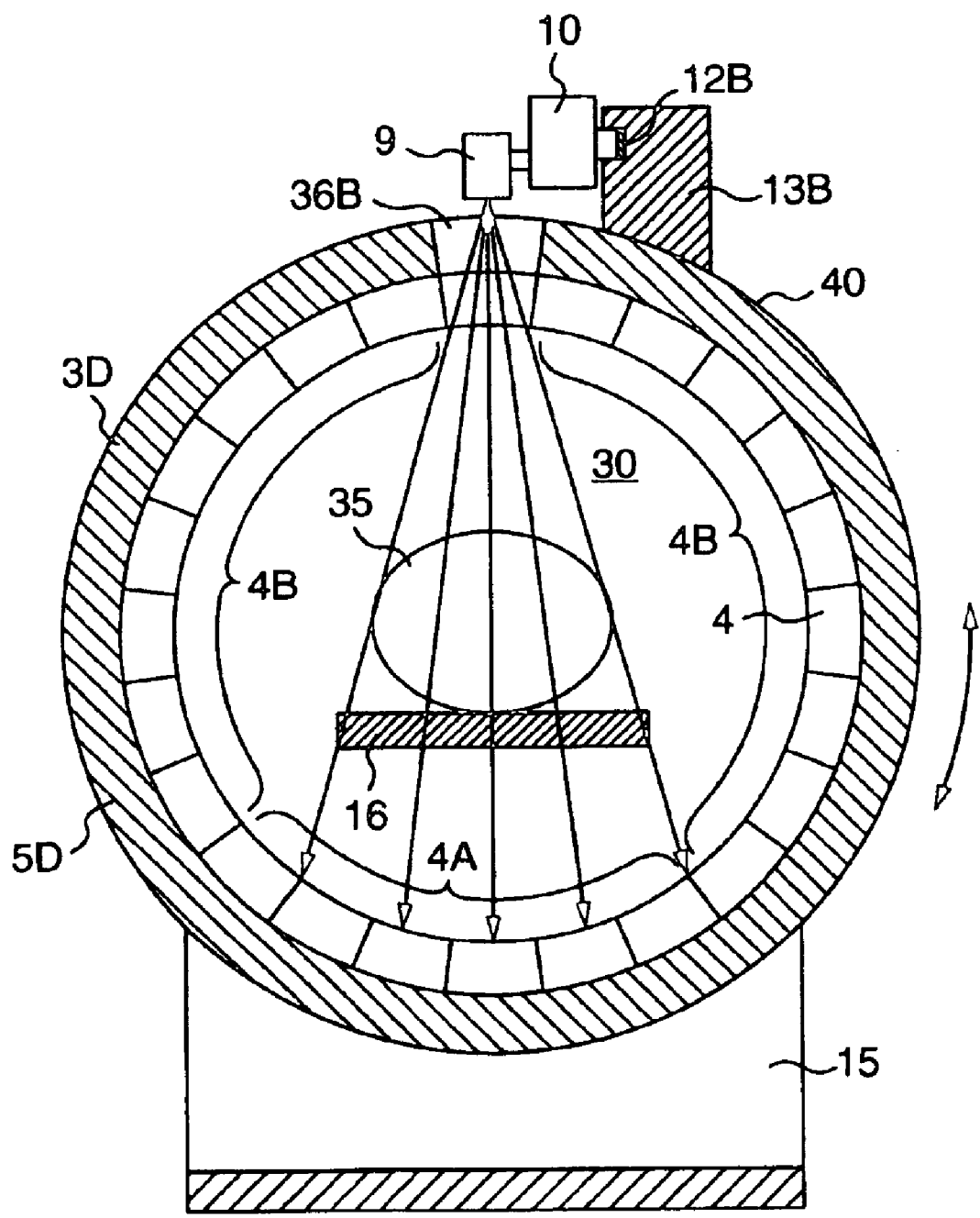
FIG. 25 is a sectional view at XXV—XXV of FIG. 24.

A radiological imaging apparatus 1J of Embodiment 12 which is another embodiment of the present invention will be explained using FIG. 24 and FIG. 25 below. In contrast to Embodiments 7 to 11 where the radiation detector ring structure is fixed, this embodiment has a configuration that the radiation detector ring structure rotates together with the X-ray source. The radiological imaging apparatus 1J has a configuration with the image pickup apparatus 2F in the radiological imaging apparatus 1F replaced with an image pickup apparatus 2J. The remaining configuration of the radiological imaging apparatus 1J is the same as that of the radiological imaging apparatus 1E. The image pickup apparatus 2J is provided with a ring-shaped rotator 40, a circumferential direction drive 41, a drive controller 17A and an X-ray source controller 18A.

The ring-shaped rotator 40 is provided with a radiation detector ring structure 3D, an X-ray source apparatus 8C and an X-ray source apparatus holding section 48. The radiation detector ring structure 3D includes radiation detectors 4 and a ring-shaped holding section 5D. As in the case of Embodiment 2, the radiation detector 4 is attached to the inner surface of the ring-shaped holding section 5D. The ring-shaped holding section 5D forms a slit 36B, which extends in the axial direction and has a rectangular cross section, at one location in the circumferential direction. No radiation detectors 4 are set in the section of the slit 36B. The X-ray source apparatus holding section 48 extends in the axial direction and is placed on the outer surface of the ring-shaped holding section 5D. The X-ray source apparatus 8C of this embodiment has a configuration similar to that of Embodiment 11. The X-ray source drive 10 of the X-ray source apparatus 8C moves along the guide rail 12B provided for the X-ray source apparatus holding section 48. Thus, the X-ray source 9 moves in the axial direction of the radiation detector ring structure 3D.

Figure 26:
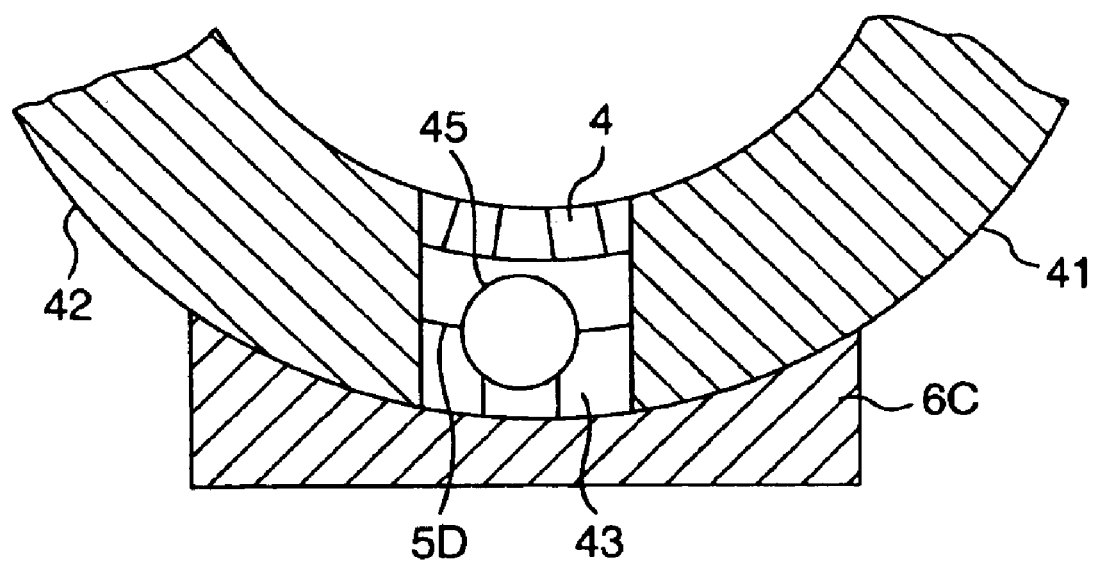
FIG. 26 is a sectional view at XXVI—XXVI of FIG. 24.

The circumferential direction drive 41 includes a practically ring-shaped rotator holding section 42 and a drive unit 44. The rotator holding section 42 is mounted on a support 6C fixed to the floor as shown in FIG. 26. Part of the area contacting the support 6C of the rotator holding section 42 is incised, forming a space 43 as shown in FIG. 26. The drive unit 44 is placed inside the space 43. The drive unit 44 includes a motor 45, a reduction gear unit 46 connected to the rotational axis of the motor 45 and a pinion 47 connected to the reduction gear unit 46. The motor 45 and the reduction gear unit 46 are mounted on the support 6C. The rotator holding section 42 includes a practically ring-shaped guide groove 49 on one end face facing the ring-shaped rotator 40. The support 15 also includes an arc-shaped guide groove 50 on one end face facing the ring-shaped rotator 40. One end of the ring-shaped holding section 5D is inserted into the guide groove 49 and the other end is inserted in the guide groove 50. A rack (not shown) is provided on the outer surface at the end on the rotator holding section 42 side of the ring-shaped holding section 5D. This rack is engaged with the pinion 47. The ring-shaped rotator 40 with the end of the ring-shaped holding section 5D inserted in the guide grooves 49 and 50 is supported by the support 15 and rotator holding section 42.

This embodiment carries out X-ray computed tomographic inspection and PET inspection by rotating the ring-shaped rotator 40. When both inspections are carried out, both the radiation detector 4 and X-ray source 9 rotate in the circumferential direction. At the start of an inspection, the motor 45 is driven, its rotational force is transmitted to the pinion 47 via the reduction gear unit 46. When the pinion 47 rotates, the ring-shaped holding section 5D rotates guided by the guide grooves 49 and 50. The ring-shaped rotator 40 rotates in this way. While the ring-shaped rotator 40 is rotating, X-rays are radiated from the X-ray source 9. The collimator (not shown) mounted on the X-ray source 9 suppresses the spread of X-rays in the axial direction of the through hole section 30 and forms fan-shaped X-rays in the circumferential direction.

Since both the radiation detector 4 and X-ray source 9 rotate in the circumferential direction in this embodiment, the position of the radiation detector 4 which detects X-rays does not change as in the case of Embodiments 7 to 11. That is, when the X-ray source 9 rotates, a plurality of radiation detectors 4 (called "radiation detectors 4A", see FIG. 25) located in specific positions within the radiation detector ring structure 3D always detect X-rays passing through the examinee 35. These radiation detectors 4A also detect γ-rays radiated from the examinee 35 and output both X-ray image pickup signals and γ-ray image pickup signals. The signal discriminators 19 connected to the radiation detectors 4A perform processing of X-ray image pickup signals and γ-ray image pickup signals as in the case of Embodiment 8. The radiation detectors 4 other than the radiation detectors 4A (called "radiation detectors 4B", see FIG. 25) detect γ-rays but not X-rays. The radiation detectors 4B do not output X-ray image pickup signals, but output γ-ray image pickup signals. Thus, the signal discriminators 19 connected to the radiation detectors 4B are not provided with any pulse height analyzer 38 to process X-ray image pickup signals, which simplifies the structure. The signal discriminators 19 connected to the radiation detectors 4B process γ-ray image pickup signals. The computer 27 in this embodiment executes the processing shown in FIG. 5 to create fused tomographic image data.

This embodiment produces the effects (2) to (4) in Embodiment 7, the effects (9) and (10) in Embodiment 8 and effects (11) and (13) in Embodiment 9. This embodiment can further produce the following effect (16). In this embodiment, the collimator used in Embodiment 11 can also be set on the outlet side of the slit 36B. Installing this collimator produces the effect (14) obtained in Embodiment 11.

(16) In this embodiment, a plurality of radiation detectors 4 is arranged in a ring form on the rotating radiation detector ring structure 3. This embodiment allows some of radiation detectors 4 arranged in a ring form to detect a plurality of γ-ray pairs radiated from the examinee 35 who is a test subject and also detect X-rays radiated from the X-ray source 9 moving in the circumferential direction and passing through the examinee 35. Thus, this embodiment only needs one image pickup apparatus as in the case of Embodiment 7, thus simplifying the configuration of the radiological imaging apparatus capable of executing both X-ray computed tomographic inspection and PET inspection.

This embodiment has a configuration with the slit 36B having an elongated rectangular cross section in the axial direction of the radiation detector ring structure allowing the X-ray source 9 to move in the axial direction, but this embodiment is not limited to this configuration and it is also possible to form a minimum slit that matches the beam form of the X-ray source, for example. This configuration eliminates the need for the axial transfer mechanism of the X-ray source (X-ray source apparatus holding section 48, etc. having the guide rails 12B). In this case, it is possible to move the examinee 35 in the axial direction with the bed 16.

While fan-beam shaped X-rays are irradiated in Embodiments 1 to 12, irradiation of X-rays is not limited to this. It is also possible to irradiate cone-beam-shaped X-rays to obtain three-dimensional fused tomographic image data, for example. While semiconductor radiation detectors using CdTe are used as the radiation detectors 4 in Embodiments 1 to 12, it is also possible to use semiconductor radiation detectors using CZT and GaAs, etc. In Embodiments 1 to 12, it is also possible to use a scintillator which is a radiation detector other than semiconductor radiation detector. As the crystal of the scintillator, bismuth germanate, gadolinium silicate or yttrium silicate are used. Use of the scintillator as a radiation detector further reduces the inspection time in each embodiment. In Embodiments 1 to 12, the X-ray source or the X-ray source and radiation detectors are rotated around the test subject, but it is also possible to fix the X-ray source and radiation detectors and rotate the test subject.

In Embodiments 1 to 12, inspection on the test subject in the axial direction of the through hole section 30 is performed by moving the bed 16. However, this inspection can also be performed with the bed 16 fixed and by moving the image pickup apparatus in the axial direction. Furthermore, in Embodiments 1 to 12, the radiation detectors are placed in a cylindrical form, but the arrangement of the radiation detectors is not limited to this. For example, it is also possible to adopt various configurations, for example, by combining six flat panels provided with radiation detectors arranging them in a hexahedron form.

It should be further understood by those skilled in the art that the foregoing description has been made on embodiments of the invention and that various changes and modifications may be made in the invention without departing from the spirit of the invention and the scope of the appended claims.

What is claimed is:

1. A radiological imaging apparatus comprising:
    an X-ray source that radiates X-rays;
    a first X-ray source transfer apparatus for rotating said X-ray source around a bed supporting a test subject;
    a plurality of radiation detectors that output both a first detection signal which is a detection signal of said X-rays that have passed through said test subject and a second detection signal which is a detection signal of γ-rays radiated from said test subject; and
    a second X-ray source transfer apparatus for moving said X-ray source in a longitudinal direction of said bed between said radiation detectors and said bed.

2. The radiological imaging apparatus according to claim 1, further comprising a tomographic image data creation apparatus that creates first tomographic image data of said test subject based on said first detection signal, creates second tomographic image data of said test subject based on said second detection signal and creates fused tomographic image data combining said first tomographic image data and said second tomographic image data.

3. The radiological imaging apparatus according to claim 1, further comprising a controller that instructs said X-ray source to radiate and stop radiating X-rays alternately and to radiate X-rays for a set time.

4. The radiological imaging apparatus according to claim 1, wherein said radiation detector is either a semiconductor radiation detector or a scintillator.

5. The radiological imaging apparatus according to claim 1, wherein an image pickup apparatus is provided with a collimator placed facing said radiation detectors arranged in a ring form and said collimator is placed inside said radiation detectors.

6. A radiological imaging apparatus comprising:
    an X-ray source that radiates X-rays;

a first X-ray source transfer apparatus for rotating said X-ray source around a bed supporting a test subject;

a plurality of radiation detectors that output an output signal including a first detection signal which is a detection signal of said X-rays that have passed through a test subject and a second detection signal which is a detection signal of γ-rays radiated from said test subject; and a second X-ray source transfer apparatus for moving said X-ray source in a longitudinal direction of said bed between said radiation detectors and said bed.

7. The radiological imaging apparatus according to claim 6, further comprising a plurality of signal discriminators connected to said respective radiation detectors, which separate said first detection signal and said second detection signal from said output signal entered.

8. The radiological imaging apparatus according to claim 6, further comprising a tomographic image data creation apparatus that creates first tomographic image data of said test subject based on said first detection signal, creates second tomographic image data of said test subject based on said second detection signal and creates fused tomographic image data combining said first tomographic image data and said second tomographic image data.

9. The radiological imaging apparatus according to claim 6, wherein said radiation detector is either a semiconductor radiation detector or a scintillator.

10. A radiological imaging apparatus comprising:

an X-ray source that radiates X-rays;

a first X-ray source transfer apparatus for rotating said X-ray source around a bed supporting a test subject;

a plurality of first radiation detectors that output an output signal including a first detection signal which is a detection signal of said X-rays that have passed through a test subject and a second detection signal which is a detection signal of γ-rays radiated from said test subject;

a plurality of second radiation detectors that output an output signal including a first detection signal which is the detection signal of said X-rays and a second detection signal which is the detection signal of said γ-rays;

a signal processor that calculates an intensity of said first detection signal based on the output signal of said first radiation detector;

a signal discriminator that separates said second detection signal from the output signal of said second radiation detector; and a counter that calculates a count rate for the second detection signal separated by said signal discriminator; and a second X-ray source transfer apparatus for moving said X-ray source in a longitudinal direction of said bed between said first and second radiation detectors and said bed.

11. The radiological imaging apparatus according to claim 10, further comprising a tomographic image data creation apparatus that creates first tomographic image data of said test subject based on the intensity of said first detection signal, creates second tomographic image data of said test subject based on the count rate of said second detection signal and creates fused tomographic image data combining said first tomographic image data and said second tomographic image data.

12. A radiological imaging apparatus comprises:

a test subject holding apparatus provided with a bed which is movable in a longitudinal direction to carry a test subject; and an image pickup apparatus.

wherein said image pickup apparatus comprises:

a radiation detector ring structure that surrounds an area in which said bed is inserted and includes a plurality of radiation detectors;

an X-ray source that irradiates said test subject with X-rays; and a first X-ray source transfer apparatus that transfers said X-ray source in the circumferential direction of said radiation detector ring structure; and a second X-ray source transfer apparatus for moving said X-ray source in a longitudinal direction of said bed between said radiation detectors and said bed, and said respective radiation detectors output both a first detection signal which is the detection signal of said X-rays that have passed through said test subject and a second detection signal which is the detection signal of γ-rays radiated from said test subject.

13. The radiological imaging apparatus according to claim 12, further comprising a tomographic image data creation apparatus that creates first tomographic image data of said test subject based on said first detection signal, creates second tomographic image data of said test subject based on said second detection signal and creates fused tomographic image data combining said first tomographic image data and said second tomographic image data.

14. The radiological imaging apparatus according to claim 12, further comprising an X-ray source controller that instructs said X-ray source apparatus to radiate and stop radiating X-rays alternately and to radiate X-rays for a set time.

15. The radiological imaging apparatus according to claim 14, further comprising for each of said radiation detectors:

a first signal processor that processes said first detection signal;

a second signal processor that processes said second detection signal;

a signal processor provided with a switching apparatus that transmits said first detection signal from said radiation detectors to said first signal processor and transmits said second detection signal from said radiation detectors to said second signal processor; and a switching control apparatus that controls said switching apparatus so that said first detection signal output from said radiation detector selected according to the position of said X-ray source transfer apparatus in the circumferential direction of said radiation detector ring structure is transmitted to said first signal processor.

16. The radiological imaging apparatus according to claim 15, further comprising a tomographic image data creation apparatus that creates first tomographic image data of said test subject based on the output of said first signal processor, creates second tomographic image data of said test subject based on the output of said second signal processor and creates fused tomographic image data combining said first tomographic image data and said second tomographic image data.

17. The radiological imaging apparatus according to claim 15, further comprising an X-ray source controller that instructs said X-ray source apparatus to radiate and stop radiating X-rays alternately and to radiate X-rays for a set time.

18. The radiological imaging apparatus according to claim 12, wherein said image pickup apparatus comprises a collimator placed facing each of said radiation detectors and said collimator is located inside said radiation detector ring structure.

19. The radiological imaging apparatus according to claim 18, further comprising a collimator transfer apparatus that transfers said collimator in the axial direction of said radiation detector ring structure.

20. The radiological imaging apparatus according to claim 12, wherein said radiation detector is either a semiconductor radiation detector or scintillator.

21. A radiological imaging apparatus comprising:
   a test subject holding apparatus provided with a bed which is movable in a longitudinal direction to carry a test subject;
   and an image pickup apparatus,
   wherein said image pickup apparatus comprises:
   a radiation detector ring structure that surrounds an area in which said bed is inserted and includes a plurality of radiation detectors;
   an X-ray source that irradiates said test subject with X-rays;
   a first X-ray source transfer apparatus that transfers said X-ray source in the circumferential direction of said radiation detector ring structure;
   a second X-ray source transfer apparatus for moving said X-ray source in a longitudinal direction of said bed between said radiation detectors and said bed; and
   said respective radiation detectors output an output signal including a first detection signal which is the detection signal of said X-rays that have passed through said test subject and a second detection signal which is the detection signal of γ-rays radiated from said test subject.

22. The radiological imaging apparatus according to claim 21, further comprising a signal discriminator which separates said first detection signal and said second detection signal from said output signal entered and which is connected to each of said plurality of radiation detectors.

23. The radiological imaging apparatus according to claim 22, further comprising said signal discriminator that separates said first detection signal and said second detection signal based on energy of said output signal.

24. The radiological imaging apparatus according to claim 22, further comprising a tomographic image data creation apparatus that creates first tomographic image data of said test subject based on said first detection signal, creates second tomographic image data of said test subject based on said second detection signal and creates fused tomographic image data combining said first tomographic image data and said second tomographic image data.

25. The radiological imaging apparatus according to claim 21, wherein said image pickup apparatus comprises a collimator placed facing each of said radiation detectors and said collimator is located inside said radiation detector ring structure.

26. The radiological imaging apparatus according to claim 25, further comprising a collimator transfer apparatus that transfers said collimator in the axial direction of said radiation detector ring structure.

27. The radiological imaging apparatus according to claim 21, wherein said radiation detector is either a semiconductor radiation detector or scintillator.

* * * * *